(12) United States Patent
Yasukawa et al.

(10) Patent No.: US 11,932,699 B2
(45) Date of Patent: Mar. 19, 2024

(54) AQUEOUS PHARMACEUTICAL COMPOSITION

(71) Applicant: JCR Pharmaceuticals Co., Ltd., Ashiya (JP)

(72) Inventors: Hidehito Yasukawa, Kobe (JP); Yuka Yamaguchi, Kobe (JP); Shinji Okabe, Kobe (JP)

(73) Assignee: JCR Pharmaceuticals Co., Ltd., Ashiya (JP)

(*) Notice: Subject to any disclaimer, the term of this patent is extended or adjusted under 35 U.S.C. 154(b) by 923 days.

(21) Appl. No.: 16/644,355

(22) PCT Filed: Sep. 7, 2018

(86) PCT No.: PCT/JP2018/033143
§ 371 (c)(1),
(2) Date: Mar. 4, 2020

(87) PCT Pub. No.: WO2019/049967
PCT Pub. Date: Mar. 14, 2019

(65) Prior Publication Data
US 2021/0061918 A1   Mar. 4, 2021

(30) Foreign Application Priority Data

Sep. 7, 2017   (JP) ................................ 2017-172156

(51) Int. Cl.
| | | |
|---|---|---|
| *A61K 39/395* | (2006.01) | |
| *A61K 9/08* | (2006.01) | |
| *C07K 16/28* | (2006.01) | |
| *C12N 9/16* | (2006.01) | |
| *A61K 39/00* | (2006.01) | |

(52) U.S. Cl.
CPC .......... *C07K 16/2881* (2013.01); *A61K 9/08* (2013.01); *C12N 9/16* (2013.01); *A61K 2039/505* (2013.01); *C12Y 301/06013* (2013.01)

(58) Field of Classification Search
None
See application file for complete search history.

(56) References Cited

U.S. PATENT DOCUMENTS

| | | | | |
|---|---|---|---|---|
| 10,940,185 B2 * | 3/2021 | Yasukawa | ............... | A61P 25/00 |
| 11,248,045 B2 * | 2/2022 | Sonoda | ............. | C07K 14/7151 |
| 2008/0200656 A1 * | 8/2008 | Sek | .......................... | A61K 9/10 |
| | | | | 530/390.5 |
| 2012/0003202 A1 | 1/2012 | Calias et al. | | |
| 2015/0313996 A1 | 11/2015 | Park et al. | | |
| 2016/0152719 A1 | 6/2016 | Pardridge et al. | | |
| 2016/0369001 A1 | 12/2016 | Sonoda et al. | | |
| 2017/0202909 A1 | 7/2017 | Haqq et al. | | |
| 2018/0171012 A1 * | 6/2018 | Sonoda | ................ | C07K 14/475 |
| 2019/0225700 A1 | 7/2019 | Koshimura et al. | | |
| 2019/0336586 A1 | 11/2019 | Yasukawa et al. | | |

FOREIGN PATENT DOCUMENTS

| | | | | |
|---|---|---|---|---|
| CN | 102946858 A | 2/2013 | | |
| CN | 103096918 A | 5/2013 | | |
| CN | 104870019 A | 8/2015 | | |
| CN | 107074931 A | 8/2017 | | |
| JP | 2000-508665 A | 7/2000 | | |
| JP | 2005-527470 A | 9/2005 | | |
| JP | 2013-534526 A | 9/2013 | | |
| JP | 2016-502528 A | 1/2016 | | |
| JP | 2017-519009 A | 7/2017 | | |
| WO | WO 97/39768 A1 | 10/1997 | | |
| WO | WO 03/020299 A1 | 3/2003 | | |
| WO | WO 2011/141926 A2 | 11/2011 | | |
| WO | WO 2011/163648 A1 | 12/2011 | | |
| WO | WO 2015/192127 A2 | 12/2015 | | |
| WO | WO 2016/208695 A1 | 12/2016 | | |
| WO | WO-2016208695 A1 * | 12/2016 | ........... | A61K 38/465 |
| WO | WO 2018/038243 A1 | 3/2018 | | |
| WO | WO 2018/124277 A1 | 7/2018 | | |

OTHER PUBLICATIONS

Extended European Search Report dated May 17, 2021 in European Patent Application No. 18853124.8, 8 pages.
International Search Report dated Nov. 13, 2018 in PCT/JP2018/033143 filed on Sep. 7, 2018, 2 pages.
Elaprase (registered trademark) intravenous drip infusion 6mg, Jul. 2016, 9 total pages (with English translation).
Actemra (registered trademark) intravenous drip infusion 80mg/ Actemra (registered trademark) intravenous drip infusion 200mg/ Actemra (registered trademark) intravenous drip infusion 400mg, Nov. 2016, 20 total pages (with English translation).

\* cited by examiner

*Primary Examiner* — Michael Szperka
(74) *Attorney, Agent, or Firm* — Oblon, McClelland, Maier & Neustadt, L.L.P.

(57) ABSTRACT

Aqueous pharmaceutical compositions containing a fusion protein of an antibody and a lysosomal enzyme as an active ingredient, which are stable enough to be marketed, are disclosed. The aqueous pharmaceutical composition, for example, comprises the fusion protein of the antibody and the lysosomal enzyme at a concentration of 0.5 to 20 mg/mL, sodium chloride at a concentration of 0.3 to 1.2 mg/mL, sucrose at a concentration of 50 to 100 mg/mL, a nonionic surfactant at a concentration of 0.15 to 3 mg/mL, a buffer at a concentration of 3 to 30 mM, and is adjusted to pH 5.0 to 7.5.

1 Claim, 4 Drawing Sheets

Specification includes a Sequence Listing.

```
                        SEQUENCE LISTING

<160> NUMBER OF SEQ ID NOS: 28

<210> SEQ ID NO 1
<211> LENGTH: 525
<212> TYPE: PRT
<213> ORGANISM: Homo sapiens

<400> SEQUENCE: 1

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190
```

```
Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
        515                 520                 525

<210> SEQ ID NO 2
<211> LENGTH: 214
<212> TYPE: PRT
<213> ORGANISM: Artificial Sequence
<220> FEATURE:
<223> OTHER INFORMATION: amino acid sequence of the light-chain of
      humanized anti-hTfR antibody No. 1

<400> SEQUENCE: 2

Asp Ile Gln Val Thr Gln Ser Pro Ser Phe Leu Ser Ala Ser Val Gly
1               5                   10                  15

Asp Arg Val Thr Ile Thr Cys Lys Ala Ser Gln Asp Val Asn Ser Ala
            20                  25                  30
```

Val Ala Trp Phe Gln Gln Lys Pro Gly Lys Ala Pro Lys Leu Leu Ile
            35                  40                  45

Tyr Trp Thr Ser Thr Arg His Thr Gly Val Pro Asp Arg Phe Ser Gly
     50                  55                  60

Ser Gly Ser Gly Thr Val Tyr Thr Leu Thr Ile Ser Ser Leu Gln Pro
 65                  70                  75                  80

Glu Asp Phe Ala Thr Tyr Tyr Cys Gln Gln His Tyr Ser Thr Pro Arg
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 3
<211> LENGTH: 725
<212> TYPE: DNA
<213> ORGANISM: Artificial Sequence
<220> FEATURE:
<223> OTHER INFORMATION: nucleotide seuquence encoding amino acid
      sequence of the light-chain of humanized anti-hTfR antibody No. 1,
      synthetic sequence

<400> SEQUENCE: 3
acgcgtgccg ccaccatggg ctggagctgg attctgctgt tcctcctgag cgtgacagca      60
ggagtgcaca gcgacatcca ggtcacacag tcaccaagtt ttctgagcgc aagcgtgggc    120
gacagggtca ctatcacatg caaggcaagc caggacgtga actccgcagt ggcctggttc    180
cagcagaagc cagggaaagc acccaagctg ctgatctatt ggacctctac aaggcacacc    240
ggtgtcccag atcggttctc aggttccggc agcggaacag tgtatactct gaccatttcc    300
agcctgcagc ctgaagactt cgctacttac tattgccagc agcattactc caccccaaga    360
acatttggcg gagggactaa agtggagatc aagaggaccg tggccgctcc ctccgtcttc    420
atttttcccc ctagcgacga acagctgaag agtggcacag cctcagtggt ctgtctgctg    480
aacaatttct accctaggga ggctaaagtg cagtggaagg tcgataacgc actgcagtct    540
ggaaatagtc aggagtcagt gacagaacag gactccaaag atagcactta ttctctgtct    600
agtacactga ctctgagcaa ggccgattac gaaaagcaca agtgtatgc ttgcgaagtc    660 acccatcagg ggctgtcatc accagtcacc aagtcattca atagaggcga gtgctaagcg    720
gccgc                                                               725

<210> SEQ ID NO 4
<211> LENGTH: 214
<212> TYPE: PRT

<213> ORGANISM: Artificial Sequence
<220> FEATURE:
<223> OTHER INFORMATION: amino acid sequence of the light-chain of humanized anti-hTfR antibody No. 2

<400> SEQUENCE: 4

```
Glu Ile Val Leu Thr Gln Ser Pro Asp Phe Gln Ser Val Thr Pro Lys
1               5                   10                  15
Glu Lys Val Thr Ile Thr Cys Arg Ala Ser Gln Ser Ile Ser Asn Asn
            20                  25                  30
Leu Gln Trp Tyr Gln Gln Lys Pro Asp Gln Ser Pro Lys Leu Leu Ile
        35                  40                  45
Lys Tyr Ala Ser Gln Ser Ile Ser Gly Ile Pro Ser Arg Phe Ser Gly
    50                  55                  60
Ser Gly Ser Gly Thr Asp Phe Thr Leu Thr Ile Asn Ser Leu Glu Ala
65                  70                  75                  80
Glu Asp Ala Ala Thr Tyr Leu Cys Gln Gln Ser Asn Ser Trp Pro Arg
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 5
<211> LENGTH: 725
<212> TYPE: DNA
<213> ORGANISM: Artificial Sequence
<220> FEATURE:
<223> OTHER INFORMATION: nucleotide sequence encoding amino acid sequence of the light-chain of humanized anti-hTfR antibody No. 2, synthetic sequence

<400> SEQUENCE: 5

```
acgcgtgccg ccaccatggg ctggagctgg attctgctgt tcctcctgag cgtgacagca      60
ggagtgcaca gcgaaattgt gctgacccag tctcccgatt tccagtccgt gaccccaag     120
gagaaagtca ccatcacatg cagagcatca cagtccatta gcaacaatct gcagtggtac     180
cagcagaagc cagaccagag ccccaagctg ctgatcaaat atgcctctca gagtatttca     240
ggcataccct ctaggttctc cggtagcggc tctggaaccg acttactct gaccatcaac     300
agtctggagg ctgaagatgc cgctacatac ttgtgccagc agagtaattc atggcctagg     360
acctttggcc aggggacaaa ggtggagatc aaaaggactg tggcagcccc aagtgtcttc     420
attttccccc cttcagacga acagctgaag agcggcacag catctgtggt ctgtctgctg     480
aacaatttct acccacggga ggctaaggtg cagtggaaag tcgataacgc actgcagtcc     540
```

```
ggaaatagcc aggagtctgt gactgaacag gacagtaagg attcaaccta ttccctgtcc    600
agcacactga ctctgagcaa agccgattac gagaagcaca agtgtatgc ttgcgaagtc     660 acacatcagg ggctgtctag tcccgtgact aagtctttta atagggggtga atgttaagcg   720 gccgc                                                                725
```

<210> SEQ ID NO 6
<211> LENGTH: 219
<212> TYPE: PRT
<213> ORGANISM: Artificial Sequence
<220> FEATURE:
<223> OTHER INFORMATION: amino acid sequence of the light-chain of
      humanized anti-hTfR antibody No. 3

<400> SEQUENCE: 6

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 7
<211> LENGTH: 740
<212> TYPE: DNA
<213> ORGANISM: Artificial Sequence
<220> FEATURE:
<223> OTHER INFORMATION: nucleotide seuquence encoding amino acid
      sequence of the light-chain of humanized anti-hTfR antibody No. 3,
      synthetic sequence

<400> SEQUENCE: 7

```
acgcgtgccg ccaccatggg ctggagctgg attctgctgt tcctcctgag cgtgacagca    60
ggagtgcaca gcgacatcgt gatgacccag actcccctga gcctgagcgt gacacctggc    120
cagcctgcca gcatcagctg cagaagctct cagagcctgg tgcacagcaa cggcaacacc   180
```

```
tacctgcact ggtatctgca gaagcccggc cagagccctc agctgctgat ctacaaggtg      240
tccaacagat tcagcggcgt gcccgacaga ttctccggca gcggctctgg caccgacttc      300
accctgaaga tttccagagt ggaagccgag gacgtgggcg tgtactactg cagccagagc      360
acccacgtgc cctggacatt cggccagggc accaaggtgg aaatcaagag aaccgtggcc      420
gctcccagcg tgttcatctt cccacctagc gacgagcagc tgaagtccgg cacagcctct      480
gtcgtgtgcc tgctgaacaa cttctacccc cgcgaggcca aggtgcagtg gaaggtggac      540
aacgccctgc agagcggcaa cagccaggaa agcgtgaccg agcaggactc caaggacagc      600
acctacagcc tgagcagcac cctgaccctg agcaaggccg actacgagaa gcacaaggtg      660
tacgcctgcg aagtgaccca ccagggcctg tctagccccg tgaccaagag cttcaacaga      720
ggcgagtgct aagcggccgc                                                  740
```

<210> SEQ ID NO 8
<211> LENGTH: 446
<212> TYPE: PRT
<213> ORGANISM: Artificial Sequence
<220> FEATURE:
<223> OTHER INFORMATION: amino acid sequence of the heavy-chain of humanized anti-hTfR antibody No. 1

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Tyr
            20                  25                  30

Gly Met Ser Trp Val Arg Gln Ala Pro Gly Lys Gly Leu Glu Leu Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Asn Asn Arg Tyr Asp Glu Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255
```

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 9
<211> LENGTH: 453
<212> TYPE: PRT
<213> ORGANISM: Artificial Sequence
<220> FEATURE:
<223> OTHER INFORMATION: amino acid sequence of the heavy-chain of
      humanized anti-hTfR antibody No. 2

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Gly Leu Glu Trp Ile
        35                  40                  45

Gly Val Ile Ser Thr Tyr Tyr Gly His Gly Ser Tyr Asn Gln Arg Phe
    50                  55                  60

Lys Gly Arg Ala Thr Met Thr Val Asp Lys Ser Ile Ser Thr Ala Tyr
65                  70                  75                  80

Met Glu Leu Val Arg Leu Arg Ser Asp Asp Thr Ala Val Tyr Tyr Cys
                85                  90                  95

Val Arg Gly Gly Tyr Gly Ser Ser Ser Leu Ala Gly Asn Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

```
Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 10
<211> LENGTH: 448
<212> TYPE: PRT
<213> ORGANISM: Artificial Sequence
<220> FEATURE:
<223> OTHER INFORMATION: amino acid sequence of the heavy-chain of
      humanized anti-hTfR antibody No. 3

<400> SEQUENCE: 10

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
```

```
            65                  70                  75                  80
Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 11
<211> LENGTH: 20
<212> TYPE: DNA
<213> ORGANISM: Artificial Sequence
<220> FEATURE:
<223> OTHER INFORMATION: Primer Hyg-Sfi5', synthetic sequence
```

```
<400> SEQUENCE: 11
gaggccgcct cggcctctga                                              20

<210> SEQ ID NO 12
<211> LENGTH: 29
<212> TYPE: DNA
<213> ORGANISM: Artificial Sequence
<220> FEATURE:
<223> OTHER INFORMATION: Primer Hyg-BstX3', synthetic sequence

<400> SEQUENCE: 12
aaccatcgtg atgggtgcta ttcctttgc                                    29

<210> SEQ ID NO 13
<211> LENGTH: 973
<212> TYPE: PRT
<213> ORGANISM: Artificial Sequence
<220> FEATURE:
<223> OTHER INFORMATION: amino acid sequence of fused protein of the
      heavy-chain of humanized anti-hTfR antibody No.1 and hI2S

<400> SEQUENCE: 13
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Leu | Thr | Phe | Ser | Asn | Tyr |
| | | | 20 | | | | | 25 | | | | | 30 | | |
| Gly | Met | Ser | Trp | Val | Arg | Gln | Ala | Pro | Gly | Lys | Gly | Leu | Glu | Leu | Val |
| | | 35 | | | | | 40 | | | | | 45 | | | |
| Ala | Asn | Ile | Asn | Thr | Asn | Gly | Gly | Ser | Thr | Tyr | Tyr | Pro | Asp | Ser | Val |
| 50 | | | | | 55 | | | | | 60 | | | | | |
| Lys | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Thr | Asn | Asn | Arg | Tyr | Asp | Glu | Asp | Tyr | Trp | Gly | Gln | Gly | Thr | Leu | Val |
| | | | | 100 | | | | | 105 | | | | | 110 | |
| Thr | Val | Ser | Ser | Ala | Ser | Thr | Lys | Gly | Pro | Ser | Val | Phe | Pro | Leu | Ala |
| | | | 115 | | | | | 120 | | | | | 125 | | |
| Pro | Ser | Ser | Lys | Ser | Thr | Ser | Gly | Gly | Thr | Ala | Ala | Leu | Gly | Cys | Leu |
| | 130 | | | | | 135 | | | | | 140 | | | | |
| Val | Lys | Asp | Tyr | Phe | Pro | Glu | Pro | Val | Thr | Val | Ser | Trp | Asn | Ser | Gly |
| 145 | | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 | |
| Gly | Leu | Tyr | Ser | Leu | Ser | Ser | Val | Val | Thr | Val | Pro | Ser | Ser | Ser | Leu |
| | | | 180 | | | | | 185 | | | | | 190 | | |
| Gly | Thr | Gln | Thr | Tyr | Ile | Cys | Asn | Val | Asn | His | Lys | Pro | Ser | Asn | Thr |
| | | 195 | | | | | 200 | | | | | 205 | | | |
| Lys | Val | Asp | Lys | Lys | Val | Glu | Pro | Lys | Ser | Cys | Asp | Lys | Thr | His | Thr |
| 210 | | | | | 215 | | | | | 220 | | | | | |
| Cys | Pro | Pro | Cys | Pro | Ala | Pro | Glu | Leu | Leu | Gly | Gly | Pro | Ser | Val | Phe |
| 225 | | | | | 230 | | | | | 235 | | | | | 240 |
| Leu | Phe | Pro | Pro | Lys | Pro | Lys | Asp | Thr | Leu | Met | Ile | Ser | Arg | Thr | Pro |
| | | | | 245 | | | | | 250 | | | | | 255 | |
| Glu | Val | Thr | Cys | Val | Val | Val | Asp | Val | Ser | His | Glu | Asp | Pro | Glu | Val |
| | | | 260 | | | | | 265 | | | | | 270 | | |
| Lys | Phe | Asn | Trp | Tyr | Val | Asp | Gly | Val | Glu | Val | His | Asn | Ala | Lys | Thr |

```
                275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
            325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys Gly Ser
            435                 440                 445
Ser Glu Thr Gln Ala Asn Ser Thr Thr Asp Ala Leu Asn Val Leu Leu
450                 455                 460
Ile Ile Val Asp Asp Leu Arg Pro Ser Leu Gly Cys Tyr Gly Asp Lys
465                 470                 475                 480
Leu Val Arg Ser Pro Asn Ile Asp Gln Leu Ala Ser His Ser Leu Leu
                485                 490                 495
Phe Gln Asn Ala Phe Ala Gln Gln Ala Val Cys Ala Pro Ser Arg Val
            500                 505                 510
Ser Phe Leu Thr Gly Arg Arg Pro Asp Thr Thr Arg Leu Tyr Asp Phe
            515                 520                 525
Asn Ser Tyr Trp Arg Val His Ala Gly Asn Phe Ser Thr Ile Pro Gln
530                 535                 540
Tyr Phe Lys Glu Asn Gly Tyr Val Thr Met Ser Val Gly Lys Val Phe
545                 550                 555                 560
His Pro Gly Ile Ser Ser Asn His Thr Asp Asp Ser Pro Tyr Ser Trp
                565                 570                 575
Ser Phe Pro Pro Tyr His Pro Ser Ser Glu Lys Tyr Glu Asn Thr Lys
            580                 585                 590
Thr Cys Arg Gly Pro Asp Gly Glu Leu His Ala Asn Leu Leu Cys Pro
            595                 600                 605
Val Asp Val Leu Asp Val Pro Glu Gly Thr Leu Pro Asp Lys Gln Ser
            610                 615                 620
Thr Glu Gln Ala Ile Gln Leu Leu Glu Lys Met Lys Thr Ser Ala Ser
625                 630                 635                 640
Pro Phe Phe Leu Ala Val Gly Tyr His Lys Pro His Ile Pro Phe Arg
                645                 650                 655
Tyr Pro Lys Glu Phe Gln Lys Leu Tyr Pro Leu Glu Asn Ile Thr Leu
            660                 665                 670
Ala Pro Asp Pro Glu Val Pro Asp Gly Leu Pro Pro Val Ala Tyr Asn
            675                 680                 685
Pro Trp Met Asp Ile Arg Gln Arg Glu Asp Val Gln Ala Leu Asn Ile
            690                 695                 700
```

| | | | | | | | | | | | |
|---|---|---|---|---|---|---|---|---|---|---|---|
| Ser | Val | Pro | Tyr | Gly | Pro | Ile | Pro | Val | Asp | Phe | Gln | Arg | Lys | Ile | Arg |
| 705 | | | | | 710 | | | | | 715 | | | | | 720 |

Ser Val Pro Tyr Gly Pro Ile Pro Val Asp Phe Gln Arg Lys Ile Arg
705                 710                 715                 720

Gln Ser Tyr Phe Ala Ser Val Ser Tyr Leu Asp Thr Gln Val Gly Arg
            725                 730                 735

Leu Leu Ser Ala Leu Asp Asp Leu Gln Leu Ala Asn Ser Thr Ile Ile
            740                 745                 750

Ala Phe Thr Ser Asp His Gly Trp Ala Leu Gly Glu His Gly Glu Trp
            755                 760                 765

Ala Lys Tyr Ser Asn Phe Asp Val Ala Thr His Val Pro Leu Ile Phe
            770                 775                 780

Tyr Val Pro Gly Arg Thr Ala Ser Leu Pro Glu Ala Gly Glu Lys Leu
785                 790                 795                 800

Phe Pro Tyr Leu Asp Pro Phe Asp Ser Ala Ser Gln Leu Met Glu Pro
            805                 810                 815

Gly Arg Gln Ser Met Asp Leu Val Glu Leu Val Ser Leu Phe Pro Thr
            820                 825                 830

Leu Ala Gly Leu Ala Gly Leu Gln Val Pro Pro Arg Cys Pro Val Pro
            835                 840                 845

Ser Phe His Val Glu Leu Cys Arg Glu Gly Lys Asn Leu Leu Lys His
850                 855                 860

Phe Arg Phe Arg Asp Leu Glu Glu Asp Pro Tyr Leu Pro Gly Asn Pro
865                 870                 875                 880

Arg Glu Leu Ile Ala Tyr Ser Gln Tyr Pro Arg Pro Ser Asp Ile Pro
            885                 890                 895

Gln Trp Asn Ser Asp Lys Pro Ser Leu Lys Asp Ile Lys Ile Met Gly
            900                 905                 910

Tyr Ser Ile Arg Thr Ile Asp Tyr Arg Tyr Thr Val Trp Val Gly Phe
            915                 920                 925

Asn Pro Asp Glu Phe Leu Ala Asn Phe Ser Asp Ile His Ala Gly Glu
930                 935                 940

Leu Tyr Phe Val Asp Ser Asp Pro Leu Gln Asp His Asn Met Tyr Asn
945                 950                 955                 960

Asp Ser Gln Gly Gly Asp Leu Phe Gln Leu Leu Met Pro
            965                 970

<210> SEQ ID NO 14
<211> LENGTH: 3002
<212> TYPE: DNA
<213> ORGANISM: Artificial Sequence
<220> FEATURE:
<223> OTHER INFORMATION: nucleotide sequence encoding amino acid
      sequence of fused protein of the heavy-chain of humanized anti-
      hTfR antibody No.1 and hI2S, synthetic sequence

<400> SEQUENCE: 14

```
acgcgtgccg ccaccatggg ctggagctgg attctgctgt tcctcctgag cgtgacagca      60
ggagtgcaca gcgaagtgca gctggtcgaa tcagggggg gctggtgca gcctggaggc       120 agcctgagac tgtcctgcgc cgcttctggc ttgacctta gcaactacgg gatgtcctgg       180
gtgcggcagg ctcctggcaa gggactggag ttggtggcca acatcaatac caacggcgga     240
agtacatact atcccgattc agtgaagggc cggttcacca tcagcaggga caacgccaag     300
aacagcctgt atctgcagat gaactctctg agggccgagg atacagccgt gtactattgc     360
actaacaacc ggtacgacga ggactattgg ggccagggca ccctggtgac agtgtctagc     420
gcctctacca agggcccaag cgtgtttcct ctggctccat cctctaaatc cacctctggc     480
```

```
ggcacagccg ctctgggctg tctggtgaag gattacttcc cagagcccgt gacagtgtct    540
tggaacagcg gcgccctgac ctccggcgtg cacacatttc ctgctgtgct gcagagctcc    600
ggcctgtaca gcctgtctag cgtggtgacc gtgccatcct ctagcctggg cacccagaca    660
tatatctgca acgtgaatca caagcccagc aatacaaagg tggataagaa ggtggagcca    720
aagtcctgtg acaagaccca cacatgcccc ccttgtcctg ctccagagct gctgggagga    780
ccaagcgtgt tcctgtttcc acccaagccc aaggataccc tgatgatctc tcggaccccca   840 gaggtgacat gcgtggtggt ggatgtgagc cacgaggacc ccgaggtgaa gttcaactgg    900
tatgtggacg gcgtggaggt gcacaatgct aagaccaagc caggaggagga gcagtacaac   960 tccaccctata gagtggtgtc tgtgctgaca gtgctgcacc aggattggct gaacggcaag  1020
gagtataagt gcaaggtgtc caataaggcc ctgcccgctc ctatcgagaa gaccatctct   1080
aaggccaagg gccagcccag agagcctcag gtgtacacac tgcctccatc ccgggatgag   1140
ctgaccaaga accaggtgtc tctgacatgt ctggtcaagg gcttctatcc ctctgacatc   1200
gccgtggagt gggagagcaa tggccagcct gagaacaatt acaagaccac accccctgtg   1260
ctggattccg acggctcttt ctttctgtat agcaagctga ccgtggacaa gtcccggtgg   1320
cagcagggca acgtgttcag ctgttccgtg atgcacgaag ctctgcataa tcactatact   1380
cagaaatccc tgtcactgtc acctggtaaa ggatcttccg aaacgcaggc caactcgacc   1440
acagatgctc tgaacgttct tctcatcatc gtggatgacc tgcgcccctc cctgggctgt   1500 tatgggata agctggtgag gtcccccaaat attgaccaac tggcatccca cagcctcctc    1560
ttccagaatg cctttgcgca gcaagcagtg tgcgccccga gccgcgtttc tttcctcact   1620
ggcaggagac ctgacaccac ccgcctgtac gacttcaact cctactgag ggtgcacgct   1680 ggaaacttct ccaccatccc ccagtacttc aaggagaatg gctatgtgac catgtcggtg   1740
ggaaaagtct ttcaccctgg gatatcttct aaccataccg atgattctcc gtatagctgg   1800
tcttttccac cttatcatcc ttcctctgag aagtatgaaa cactaagac atgtcgaggg   1860 ccagatggag aactccatgc caacctgctt tgccctgtgg atgtgctgga tgttcccgag  1920
ggcaccttgc ctgacaaaca gagcactgag caagcctac agttgttgga aaagatgaaa   1980
acgtcagcca gtcctttctt cctggccgtt gggtatcata agccacacat ccccttcaga   2040
taccccaagg aatttcagaa gttgtatccc ttggagaaca tcaccctggc ccccgatccc   2100
gaggtccctg atggcctacc ccctgtggcc tacaaccct ggatggacat caggcaacgg    2160
gaagacgtcc aagccttaaa catcagtgtg ccgtatggtc caattcctgt ggactttcag   2220
cggaaaatcc gccagagcta ctttgcctct gtgtcatatt tggatacaca ggtcggccgc   2280
ctcttgagtg ctttggacga tcttcagctg gccaacagca ccatcattgc atttacctcg   2340
gatcatgggt gggctctagg tgaacatgga gaatgggcca aatacagcaa ttttgatgtt   2400
gctacccatg ttcccctgat attctatgtt cctggaagga cggcttcact tccgaggca   2460 ggcgagaagc ttttcccctta cctcgaccct tttgattccg cctcacagtt gatggagcca   2520
ggcaggcaat ccatgacct tgtggaactt gtgtctcttt ttcccacgct ggctggactt   2580
gcaggactgc aggttccacc tcgctgcccc gttccttcat ttcacgttga gctgtgcaga   2640
gaaggcaaga accttctgaa gcattttcga ttccgtgact ggaagaaga tccgtacctc   2700 cctggtaatc cccgtgaact gattgccat agccagtatc cccggccttc agacatccct   2760
cagtggaatt ctgacaagcc gagtttaaaa gatataaaga tcatgggcta ttccatacgc   2820
```

```
accatagact ataggtatac tgtgtgggtt ggcttcaatc ctgatgaatt tctagctaac    2880 tttctgaca tccatgcagg ggaactgtat tttgtggatt ctgacccatt gcaggatcac    2940
aatatgtata atgattccca aggtggagac cttttccagt tgttgatgcc ttaagcggcc    3000
gc                                                                  3002
```

<210> SEQ ID NO 15
<211> LENGTH: 980
<212> TYPE: PRT
<213> ORGANISM: Artificial Sequence
<220> FEATURE:
<223> OTHER INFORMATION: amino acid sequence of fused protein of the
      heavy-chain of humanized anti-hTfR antibody No.2 and hI2S

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Gly Leu Glu Trp Ile
        35                  40                  45

Gly Val Ile Ser Thr Tyr Tyr Gly His Gly Ser Tyr Asn Gln Arg Phe
    50                  55                  60

Lys Gly Arg Ala Thr Met Thr Val Asp Lys Ser Ile Ser Thr Ala Tyr
65                  70                  75                  80

Met Glu Leu Val Arg Leu Arg Ser Asp Asp Thr Ala Val Tyr Tyr Cys
                85                  90                  95

Val Arg Gly Gly Tyr Gly Ser Ser Leu Ala Gly Asn Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

```
Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Ser Ser Glu Thr Gln Ala Asn Ser Thr Thr
    450                 455                 460

Asp Ala Leu Asn Val Leu Leu Ile Ile Val Asp Asp Leu Arg Pro Ser
465                 470                 475                 480

Leu Gly Cys Tyr Gly Asp Lys Leu Val Arg Ser Pro Asn Ile Asp Gln
                485                 490                 495

Leu Ala Ser His Ser Leu Leu Phe Gln Asn Ala Phe Ala Gln Gln Ala
            500                 505                 510

Val Cys Ala Pro Ser Arg Val Ser Phe Leu Thr Gly Arg Arg Pro Asp
        515                 520                 525

Thr Thr Arg Leu Tyr Asp Phe Asn Ser Tyr Trp Arg Val His Ala Gly
    530                 535                 540

Asn Phe Ser Thr Ile Pro Gln Tyr Phe Lys Glu Asn Gly Tyr Val Thr
545                 550                 555                 560

Met Ser Val Gly Lys Val Phe His Pro Gly Ile Ser Ser Asn His Thr
                565                 570                 575

Asp Asp Ser Pro Tyr Ser Trp Ser Phe Pro Pro Tyr His Pro Ser Ser
            580                 585                 590

Glu Lys Tyr Glu Asn Thr Lys Thr Cys Arg Gly Pro Asp Gly Glu Leu
        595                 600                 605

His Ala Asn Leu Leu Cys Pro Val Asp Val Leu Asp Val Pro Glu Gly
    610                 615                 620

Thr Leu Pro Asp Lys Gln Ser Thr Glu Gln Ala Ile Gln Leu Leu Glu
625                 630                 635                 640

Lys Met Lys Thr Ser Ala Ser Pro Phe Phe Leu Ala Val Gly Tyr His
                645                 650                 655

Lys Pro His Ile Pro Phe Arg Tyr Pro Lys Glu Phe Gln Lys Leu Tyr
            660                 665                 670

Pro Leu Glu Asn Ile Thr Leu Ala Pro Asp Pro Glu Val Pro Asp Gly
        675                 680                 685

Leu Pro Pro Val Ala Tyr Asn Pro Trp Met Asp Ile Arg Gln Arg Glu
    690                 695                 700

Asp Val Gln Ala Leu Asn Ile Ser Val Pro Tyr Gly Pro Ile Pro Val
705                 710                 715                 720

Asp Phe Gln Arg Lys Ile Arg Gln Ser Tyr Phe Ala Ser Val Ser Tyr
                725                 730                 735

Leu Asp Thr Gln Val Gly Arg Leu Leu Ser Ala Leu Asp Asp Leu Gln
```

740                 745                 750
Leu Ala Asn Ser Thr Ile Ile Ala Phe Thr Ser Asp His Gly Trp Ala
            755                 760                 765
Leu Gly Glu His Gly Glu Trp Ala Lys Tyr Ser Asn Phe Asp Val Ala
            770                 775                 780
Thr His Val Pro Leu Ile Phe Tyr Val Pro Gly Arg Thr Ala Ser Leu
785                 790                 795                 800
Pro Glu Ala Gly Glu Lys Leu Phe Pro Tyr Leu Asp Pro Phe Asp Ser
                805                 810                 815
Ala Ser Gln Leu Met Glu Pro Gly Arg Gln Ser Met Asp Leu Val Glu
            820                 825                 830
Leu Val Ser Leu Phe Pro Thr Leu Ala Gly Leu Ala Gly Leu Gln Val
            835                 840                 845
Pro Pro Arg Cys Pro Val Pro Ser Phe His Val Glu Leu Cys Arg Glu
        850                 855                 860
Gly Lys Asn Leu Leu Lys His Phe Arg Phe Arg Asp Leu Glu Glu Asp
865                 870                 875                 880
Pro Tyr Leu Pro Gly Asn Pro Arg Glu Leu Ile Ala Tyr Ser Gln Tyr
                885                 890                 895
Pro Arg Pro Ser Asp Ile Pro Gln Trp Asn Ser Asp Lys Pro Ser Leu
                900                 905                 910
Lys Asp Ile Lys Ile Met Gly Tyr Ser Ile Arg Thr Ile Asp Tyr Arg
            915                 920                 925
Tyr Thr Val Trp Val Gly Phe Asn Pro Asp Glu Phe Leu Ala Asn Phe
            930                 935                 940
Ser Asp Ile His Ala Gly Glu Leu Tyr Phe Val Asp Ser Asp Pro Leu
945                 950                 955                 960
Gln Asp His Asn Met Tyr Asn Asp Ser Gln Gly Gly Asp Leu Phe Gln
                965                 970                 975
Leu Leu Met Pro
            980

<210> SEQ ID NO 16
<211> LENGTH: 3023
<212> TYPE: DNA
<213> ORGANISM: Artificial Sequence
<220> FEATURE:
<223> OTHER INFORMATION: nucleotide seuquence encoding amino acid
      sequence of fused protein of the heavy-chain of humanized anti-
      hTfR antibody No.2 and hI2S, synthetic sequence

<400> SEQUENCE: 16
acgcgtgccg ccaccatggg ctggagctgg attctgctgt tcctcctgag cgtgacagca      60
ggagtgcaca gccaggtgca gctggtccag tcaggagccg aagtgaaaaa gcccggagcc     120
tcagtcaaag tgtcttgtaa agcatcaggt tatacattta cagactacgt catgcactgg     180
gtgaggcagg cacctggaca gggtctggaa tggatcggcg tgatctccac ttactatggc     240
catggaagct acaaccagag attcaagggc agggcgacaa tgactgtaga caaatcaatt     300
tccactgctt atatggagct ggtaaggctg cggtccgacg ataccgctgt gtactattgc     360
gtacgaggag gatacggctc cagctctctg gctggtaatt tcgatgtgtg ggggcagggt     420
accacagtca ccgtgagttc agcaagcaca aagggcccat ctgtgtttcc actggccccc     480
tccagcaaaa gcacctctgg gggtacagcc gctctgggat gtctggtgaa ggattatttc     540
ccagagccag tcaccgtgtc ctggaacagc ggagccctga catctggagt ccacactttt     600

-continued

```
ccagctgtgc tgcagtctag tgggctgtac tccctgtcat ccgtggtcac tgtcccagc      660 tctagtctgg gtacccagac atatatctgc aacgtgaatc acaagccatc taataccaaa     720
gtcgacaaga aagtggaacc caagtcctgt gataaaactc atacctgccc ccttgtcct     780 gcaccagagc tgctgggagg accatccgtg ttcctgtttc cacccaagcc taaagacacc     840
ctgatgatta gccgaactcc cgaagtcacc tgcgtggtcg tggacgtgtc tcacgaggac     900
cctgaagtca gtttaactg gtacgtggat ggcgtcgagg tgcataatgc taagacaaaa     960 cccccgagagg aacagtacaa cagtacatat cgtgtcgtgt cagtgctgac cgtcctgcat    1020
caggactggc tgaacgggaa ggaatataag tgcaaagtgt ccaataaggc actgcccgcc    1080
cctatcgaga aaaccattag caaggccaaa ggacagccta gggaaccaca ggtgtacaca     1140
ctgcctccat cccgggacga gctgactaag aaccaggtca gcctgacctg tctggtgaaa    1200
ggcttctatc cttcagatat cgctgtggag tgggaaagta tggacagcc agagaacaat    1260 tacaagacta cccccctgt gctggactct gatgggagtt ctttctgta ttctaagctg     1320 accgtggata aaagtcggtg gcagcagggt aatgtcttta gttgttcagt gatgcacgaa    1380
gcactgcaca accactacac ccagaaatca ctgtcactgt caccagggaa aggatcttcc    1440
gaaacgcagg ccaactcgac cacagatgct ctgaacgttc ttctcatcat cgtggatgac    1500
ctgcgcccct ccctgggctg ttatggggat aagctggtga ggtccccaaa tattgaccaa    1560
ctggcatccc acagcctcct cttccagaat gcctttgcgc agcaagcagt gtgcgccccg    1620
agccgcgttt cttcctcac tggcaggaga cctgacacca cccgcctgta cgacttcaac    1680
tcctactgga gggtgcacgc tggaaacttc tccaccatcc cccagtactt caaggagaat    1740
ggctatgtga ccatgtcggt gggaaaagtc tttcaccctg ggatatcttc taaccatacc    1800
gatgattctc cgtatagctg gtcttttcca cctatcatc cttcctctga aagtatgaa     1860 aacactaaga catgtcgagg gccagatgga gaactccatg ccaacctgct ttgccctgtg    1920
gatgtgctgg atgttcccga gggcaccttg cctgacaaac agagcactga gcaagccata    1980
cagttgttgg aaaagatgaa aacgtcagcc agtcctttct tcctggccgt tgggtatcat    2040
aagccacaca tccccttcag atacccccaag gaatttcaga agttgtatcc cttggagaac    2100
atcaccctgg ccccgatcc cgaggtccct gatggcctac ccctgtggc ctacaacccc      2160 tggatggaca tcaggcaacg ggaagacgtc caagccttaa acatcagtgt gccgtatggt    2220
ccaattcctg tggactttca gcggaaaatc cgccagagct actttgcctc tgtgtcatat    2280
ttggatacac aggtcggccg cctcttgagt gctttggacg atcttcagct ggccaacagc    2340
accatcattg catttaccctc ggatcatggg tgggctctag gtgaacatgg agaatgggcc    2400
aaatacagca tttttgatgt tgctacccat gttcccctga tattctatgt tcctggaagg    2460
acggcttcac ttccggaggc aggcgagaag cttttccctt acctcgaccc ttttgattcc    2520
gcctcacagt tgatggagcc aggcaggcaa tccatggacc ttgtggaact tgtgtctctt    2580 tttccccacgc tggctggact tgcaggactg caggttccac ctcgctgccc cgttccttca    2640
tttcacgttg agctgtgcag agaaggcaag aaccttctga agcattttcg attccgtgac    2700
ttggaagaag atccgtacct ccctggtaat ccccgtgaac tgattgccta tagccagtat    2760
ccccggcctt cagacatccc tcagtggaat ctgacaagc cgagtttaaa agatataaag    2820
atcatgggct attccatacg caccatagac tataggtata ctgtgtgggt tggcttcaat    2880
cctgatgaat ttctagctaa ctttttctgac atccatgcag gggaactgta ttttgtggat    2940
tctgacccat tgcaggatca caatatgtat aatgattccc aaggtggaga ccttttccag    3000
```
ttgttgatgc cttaagcggc cgc                                              3023

<210> SEQ ID NO 17
<211> LENGTH: 975
<212> TYPE: PRT
<213> ORGANISM: Artificial Sequence
<220> FEATURE:
<223> OTHER INFORMATION: amino acid sequence of fused protein of the
      heavy-chain of humanized anti-hTfR antibody No. 3 and hI2S

<400> SEQUENCE: 17

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Met Asn Tyr
            20                  25                  30

Trp Leu Gly Trp Val Arg Gln Met Pro Gly Lys Gly Leu Glu Trp Ile
        35                  40                  45

Gly Asp Ile Tyr Pro Gly Gly Asp Tyr Pro Thr Tyr Ser Glu Lys Phe
    50                  55                  60

Lys Val Lys Ala Ile Ile Ser Ala Asp Thr Ser Ile Ser Thr Val Tyr
65                  70                  75                  80

Leu Gln Leu Ser Ser Leu Lys Ala Ser Asp Thr Ala Met Tyr Phe Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

-continued

```
Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Ser Ser Glu Thr Gln Ala Asn Ser Thr Thr Asp Ala Leu Asn Val
450                 455                 460

Leu Leu Ile Ile Val Asp Asp Leu Arg Pro Ser Leu Gly Cys Tyr Gly
465                 470                 475                 480

Asp Lys Leu Val Arg Ser Pro Asn Ile Asp Gln Leu Ala Ser His Ser
                485                 490                 495

Leu Leu Phe Gln Asn Ala Phe Ala Gln Gln Ala Val Cys Ala Pro Ser
                500                 505                 510

Arg Val Ser Phe Leu Thr Gly Arg Arg Pro Asp Thr Thr Arg Leu Tyr
            515                 520                 525

Asp Phe Asn Ser Tyr Trp Arg Val His Ala Gly Asn Phe Ser Thr Ile
        530                 535                 540

Pro Gln Tyr Phe Lys Glu Asn Gly Tyr Val Thr Met Ser Val Gly Lys
545                 550                 555                 560

Val Phe His Pro Gly Ile Ser Ser Asn His Thr Asp Asp Ser Pro Tyr
                565                 570                 575

Ser Trp Ser Phe Pro Pro Tyr His Pro Ser Ser Glu Lys Tyr Glu Asn
                580                 585                 590

Thr Lys Thr Cys Arg Gly Pro Asp Gly Glu Leu His Ala Asn Leu Leu
            595                 600                 605

Cys Pro Val Asp Val Leu Asp Val Pro Glu Gly Thr Leu Pro Asp Lys
        610                 615                 620

Gln Ser Thr Glu Gln Ala Ile Gln Leu Leu Glu Lys Met Lys Thr Ser
625                 630                 635                 640

Ala Ser Pro Phe Phe Leu Ala Val Gly Tyr His Lys Pro His Ile Pro
                645                 650                 655

Phe Arg Tyr Pro Lys Glu Phe Gln Lys Leu Tyr Pro Leu Glu Asn Ile
                660                 665                 670

Thr Leu Ala Pro Asp Pro Glu Val Pro Asp Gly Leu Pro Pro Val Ala
            675                 680                 685

Tyr Asn Pro Trp Met Asp Ile Arg Gln Arg Glu Asp Val Gln Ala Leu
        690                 695                 700

Asn Ile Ser Val Pro Tyr Gly Pro Ile Pro Val Asp Phe Gln Arg Lys
705                 710                 715                 720

Ile Arg Gln Ser Tyr Phe Ala Ser Val Ser Tyr Leu Asp Thr Gln Val
                725                 730                 735

Gly Arg Leu Leu Ser Ala Leu Asp Asp Leu Gln Leu Ala Asn Ser Thr
            740                 745                 750

Ile Ile Ala Phe Thr Ser Asp His Gly Trp Ala Leu Gly Glu His Gly
        755                 760                 765
```

| | | | | | | | | | | | | |
|---|---|---|---|---|---|---|---|---|---|---|---|---|
| Glu | Trp | Ala | Lys | Tyr | Ser | Asn | Phe | Asp | Val | Ala | Thr | His | Val | Pro | Leu |
| 770 | | | | | 775 | | | | | 780 | | |
| Ile | Phe | Tyr | Val | Pro | Gly | Arg | Thr | Ala | Ser | Leu | Pro | Glu | Ala | Gly | Glu |
| 785 | | | | | 790 | | | | | 795 | | | | | 800 |
| Lys | Leu | Phe | Pro | Tyr | Leu | Asp | Pro | Phe | Asp | Ser | Ala | Ser | Gln | Leu | Met |
| | | | | 805 | | | | | 810 | | | | | 815 |
| Glu | Pro | Gly | Arg | Gln | Ser | Met | Asp | Leu | Val | Glu | Leu | Val | Ser | Leu | Phe |
| | | | 820 | | | | | 825 | | | | | 830 |
| Pro | Thr | Leu | Ala | Gly | Leu | Ala | Gly | Leu | Gln | Val | Pro | Pro | Arg | Cys | Pro |
| | | 835 | | | | | 840 | | | | | 845 |
| Val | Pro | Ser | Phe | His | Val | Glu | Leu | Cys | Arg | Gly | Lys | Asn | Leu | Leu |
| | 850 | | | | | 855 | | | | | 860 |
| Lys | His | Phe | Arg | Phe | Arg | Asp | Leu | Glu | Glu | Asp | Pro | Tyr | Leu | Pro | Gly |
| 865 | | | | | 870 | | | | | 875 | | | | | 880 |
| Asn | Pro | Arg | Glu | Leu | Ile | Ala | Tyr | Ser | Gln | Tyr | Pro | Arg | Pro | Ser | Asp |
| | | | | 885 | | | | | 890 | | | | | 895 |
| Ile | Pro | Gln | Trp | Asn | Ser | Asp | Lys | Pro | Ser | Leu | Lys | Asp | Ile | Lys | Ile |
| | | | 900 | | | | | 905 | | | | | 910 |
| Met | Gly | Tyr | Ser | Ile | Arg | Thr | Ile | Asp | Tyr | Arg | Tyr | Thr | Val | Trp | Val |
| | | | 915 | | | | | 920 | | | | | 925 |
| Gly | Phe | Asn | Pro | Asp | Glu | Phe | Leu | Ala | Asn | Phe | Ser | Asp | Ile | His | Ala |
| 930 | | | | | 935 | | | | | 940 |
| Gly | Glu | Leu | Tyr | Phe | Val | Asp | Ser | Asp | Pro | Leu | Gln | Asp | His | Asn | Met |
| 945 | | | | | 950 | | | | | 955 | | | | | 960 |
| Tyr | Asn | Asp | Ser | Gln | Gly | Gly | Asp | Leu | Phe | Gln | Leu | Leu | Met | Pro |
| | | | 965 | | | | | 970 | | | | | 975 |

<210> SEQ ID NO 18
<211> LENGTH: 3008
<212> TYPE: DNA
<213> ORGANISM: Artificial Sequence
<220> FEATURE:
<223> OTHER INFORMATION: nucleotide seuquence encoding amino acid
    sequence of fused protein of the heavy-chain of humanized anti-
    hTfR antibody No.3 and hI2S, synthetic sequence

<400> SEQUENCE: 18

| | |
|---|---|
| acgcgtgccg ccaccatggg ctggagctgg attctgctgt tcctcctgag cgtgacagca | 60 |
| ggagtgcaca cgcgaggtgca actagtgcag tctggagcag aggtgaaaaa gcccggggag | 120 |
| tctctgaaga tcagctgtaa gggttctgga tacagcttta tgaactactg gctgggatgg | 180 |
| gtgcgccaga tgcccgggaa aggcctggag tggattgggg acatctaccc cggcggagac | 240 |
| taccctacat acagcgagaa gttcaaggtc aaggccatca tctcagccga cacgtccatc | 300 |
| agcaccgtct acctgcagtt gagcagcctg aaggcctcgg acaccgccat gtatttctgt | 360 |
| gcgagatcag gcaattacga cgaagtggcc tactggggcc aaggaaccct ggtcaccgtc | 420 |
| tcctcagcta gcaccaaggg cccatcggtc ttccccctgg caccctcctc caagagcacc | 480 |
| tctgggggca gcggccct gggctgcctg gtcaaggact acttccccga accggtgacg | 540 |
| gtgtcgtgga actcaggcgc cctgaccagc ggcgtgcaca ccttcccggc tgtcctacag | 600 |
| tcctcaggac tctactccct cagcagcgtg gtgaccgtgc cctccagcag cttgggcacc | 660 |
| cagacctaca tctgcaacgt gaatcacaag cccagcaaca ccaaggtgga caagaaagtt | 720 |
| gagcccaaat cttgtgacaa aactcacacg tgcccaccgt gcccagcacc tgaactcctg | 780 |
| gggggtccgt cagtcttcct cttccccca aaacccaagg acaccctcat gatctcccgg | 840 |

```
acccctgagg tcacatgcgt ggtggtggac gtgagccacg aagaccctga ggtcaagttc      900
aactggtacg tggacggcgt ggaggtgcat aatgccaaga caaagccgcg ggaggagcag      960
tacaacagca cgtaccgggt ggtcagcgtc ctcaccgtcc tgcaccagga ctggctgaat     1020
ggcaaggagt acaagtgcaa ggtctccaac aaagccctcc cagcccccat cgagaaaacc     1080
atctccaaag ccaaagggca gccccgagaa ccacaggtgt acaccctgcc cccatcccgg     1140
gatgagctga ccaagaacca ggtcagcctg acctgcctgg tcaaaggctt ctatcccagc     1200
gacatcgccg tggagtggga gagcaatggg cagccggaga caactacaa gaccacgcct      1260
cccgtgctgg actccgacgg ctccttcttc ctctacagca agctcaccgt ggacaagagc     1320
aggtggcagc aggggaacgt cttctcatgc tccgtgatgc atgaggctct gcacaaccac     1380
tacacgcaga agagcctctc cctgtctccg ggtaaaggat cttccgaaac gcaggccaac     1440
tcgaccacag atgctctgaa cgttcttctc atcatcgtgg atgacctgcg cccctccctg     1500
ggctgttatg gggataagct ggtgaggtcc ccaaatattg accaactggc atcccacagc     1560
ctcctcttcc agaatgcctt tgcgcagcaa gcagtgtgcg ccccgagccg cgtttctttc     1620
ctcactggca ggagacctga caccacccgc ctgtacgact tcaactccta ctggagggtg     1680
cacgctggaa acttctccac catccccag tacttcaagg agaatggcta tgtgaccatg      1740
tcggtgggaa aagtctttca ccctgggata tcttctaacc ataccgatga ttctccgtat     1800
agctggtctt ttccacctta tcatccttcc tctgagaagt atgaaaacac taagacatgt     1860
cgagggccag atggagaact ccatgccaac ctgctttgcc ctgtggatgt gctggatgtt     1920
cccgagggca ccttgcctga caaacagagc actgagcaag ccatacagtt gttggaaaag     1980
atgaaaacgt cagccagtcc tttcttcctg gccgttgggt atcataagcc acacatcccc     2040
ttcagatacc ccaaggaatt tcagaagttg tatcccttgg agaacatcac cctggccccc     2100
gatcccgagg tccctgatgg cctaccccct gtggcctaca accctggat ggacatcagg      2160
caacgggaag acgtccaagc cttaaacatc agtgtgccgt atggtccaat tcctgtggac     2220
tttcagcgga aaatccgcca gagctacttt gcctctgtgt catatttgga tacacaggtc     2280
ggccgcctct tgagtgcttt ggacgatctt cagctggcca acagcaccat cattgcattt     2340
acctcggatc atgggtgggc tctaggtgaa catggagaat gggccaaata cagcaatttt     2400
gatgttgcta cccatgttcc cctgatattc tatgttcctg aaggacggc ttcacttccg      2460
gaggcaggcg agaagctttt cccttacctc gaccttttg attccgcctc acagttgatg     2520
gagccaggca ggcaatccat ggaccttgtg gaacttgtgt ctcttttcc cacgctggct     2580
ggacttgcag gactgcaggt tccacctcgc tgccccgttc cttcatttca cgttgagctg     2640
tgcagagaag gcaagaacct tctgaagcat tttcgattcc gtgacttgga agaagatccg     2700
tacctccctg gtaatccccg tgaactgatt gcctatagcc agtatcccg gccttcagac      2760
atccctcagt ggaattctga caagccgagt ttaaaagata taaagatcat gggctattcc     2820
atacgcacca tagactatag gtatactgtg tgggttggct tcaatcctga tgaatttcta     2880
gctaactttt ctgacatcca tgcagggaa ctgtattttg tggattctga cccattgcag      2940
gatcacaata tgtataatga ttcccaaggt ggagacctt tccagttgtt gatgccttaa      3000
gcggccgc                                                              3008
```

<210> SEQ ID NO 19
<211> LENGTH: 5
<212> TYPE: PRT
<213> ORGANISM: Artificial Sequence

```
<220> FEATURE:
<223> OTHER INFORMATION: amino acid sequence of an exemplified linker 1

<400> SEQUENCE: 19

Gly Gly Gly Gly Ser
1               5

<210> SEQ ID NO 20
<211> LENGTH: 6
<212> TYPE: PRT
<213> ORGANISM: Artificial Sequence
<220> FEATURE:
<223> OTHER INFORMATION: amino acid sequence of an exemplified linker 2

<400> SEQUENCE: 20

Gly Gly Gly Gly Gly Ser
1               5

<210> SEQ ID NO 21
<211> LENGTH: 6
<212> TYPE: PRT
<213> ORGANISM: Artificial Sequence
<220> FEATURE:
<223> OTHER INFORMATION: amino acid sequence of an exemplified linker 3

<400> SEQUENCE: 21

Ser Gly Gly Gly Gly Gly
1               5

<210> SEQ ID NO 22
<211> LENGTH: 760
<212> TYPE: PRT
<213> ORGANISM: Homo sapiens

<400> SEQUENCE: 22

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
```

```
            195                 200                 205
Leu Val Tyr Leu Val Glu Asn Pro Gly Gly Tyr Val Ala Tyr Ser Lys
    210                 215                 220
Ala Ala Thr Val Thr Gly Lys Leu Val His Ala Asn Phe Gly Thr Lys
225                 230                 235                 240
Lys Asp Phe Glu Asp Leu Tyr Thr Pro Val Asn Gly Ser Ile Val Ile
                245                 250                 255
Val Arg Ala Gly Lys Ile Thr Phe Ala Glu Lys Val Ala Asn Ala Glu
                260                 265                 270
Ser Leu Asn Ala Ile Gly Val Leu Ile Tyr Met Asp Gln Thr Lys Phe
            275                 280                 285
Pro Ile Val Asn Ala Glu Leu Ser Phe Phe Gly His Ala His Leu Gly
            290                 295                 300
Thr Gly Asp Pro Tyr Thr Pro Gly Phe Pro Ser Phe Asn His Thr Gln
305                 310                 315                 320
Phe Pro Pro Ser Arg Ser Ser Gly Leu Pro Asn Ile Pro Val Gln Thr
                325                 330                 335
Ile Ser Arg Ala Ala Ala Glu Lys Leu Phe Gly Asn Met Glu Gly Asp
                340                 345                 350
Cys Pro Ser Asp Trp Lys Thr Asp Ser Thr Cys Arg Met Val Thr Ser
            355                 360                 365
Glu Ser Lys Asn Val Lys Leu Thr Val Ser Asn Val Leu Lys Glu Ile
            370                 375                 380
Lys Ile Leu Asn Ile Phe Gly Val Ile Lys Gly Phe Val Glu Pro Asp
385                 390                 395                 400
His Tyr Val Val Val Gly Ala Gln Arg Asp Ala Trp Gly Pro Gly Ala
                405                 410                 415
Ala Lys Ser Gly Val Gly Thr Ala Leu Leu Leu Lys Leu Ala Gln Met
                420                 425                 430
Phe Ser Asp Met Val Leu Lys Asp Gly Phe Gln Pro Ser Arg Ser Ile
            435                 440                 445
Ile Phe Ala Ser Trp Ser Ala Gly Asp Phe Gly Ser Val Gly Ala Thr
            450                 455                 460
Glu Trp Leu Glu Gly Tyr Leu Ser Ser Leu His Leu Lys Ala Phe Thr
465                 470                 475                 480
Tyr Ile Asn Leu Asp Lys Ala Val Leu Gly Thr Ser Asn Phe Lys Val
                485                 490                 495
Ser Ala Ser Pro Leu Leu Tyr Thr Leu Ile Glu Lys Thr Met Gln Asn
                500                 505                 510
Val Lys His Pro Val Thr Gly Gln Phe Leu Tyr Gln Asp Ser Asn Trp
            515                 520                 525
Ala Ser Lys Val Glu Lys Leu Thr Leu Asp Asn Ala Ala Phe Pro Phe
            530                 535                 540
Leu Ala Tyr Ser Gly Ile Pro Ala Val Ser Phe Cys Phe Cys Glu Asp
545                 550                 555                 560
Thr Asp Tyr Pro Tyr Leu Gly Thr Thr Met Asp Thr Tyr Lys Glu Leu
                565                 570                 575
Ile Glu Arg Ile Pro Glu Leu Asn Lys Val Ala Arg Ala Ala Ala Glu
                580                 585                 590
Val Ala Gly Gln Phe Val Ile Lys Leu Thr His Asp Val Glu Leu Asn
            595                 600                 605
Leu Asp Tyr Glu Arg Tyr Asn Ser Gln Leu Leu Ser Phe Val Arg Asp
            610                 615                 620
```

```
Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
            645                 650                 655

Thr Thr Asp Phe Gly Asn Ala Glu Lys Thr Asp Arg Phe Val Met Lys
        660                 665                 670

Lys Leu Asn Asp Arg Val Met Arg Val Glu Tyr His Phe Leu Ser Pro
    675                 680                 685

Tyr Val Ser Pro Lys Glu Ser Pro Phe Arg His Val Phe Trp Gly Ser
690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760

<210> SEQ ID NO 23
<211> LENGTH: 107
<212> TYPE: PRT
<213> ORGANISM: Artificial Sequence
<220> FEATURE:
<223> OTHER INFORMATION: amino acid sequence of the light-chain variable
      region of humanized anti-hTfR antibody No.1

<400> SEQUENCE: 23

Asp Ile Gln Val Thr Gln Ser Pro Ser Phe Leu Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Phe Gln Gln Lys Pro Gly Lys Ala Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Val Tyr Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gly Gly Thr Lys Val Glu Ile Lys
            100                 105

<210> SEQ ID NO 24
<211> LENGTH: 116
<212> TYPE: PRT
<213> ORGANISM: Artificial Sequence
<220> FEATURE:
<223> OTHER INFORMATION: amino acid sequence of the heavy-chain variable
      region of humanized anti-hTfR antibody No.1

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Tyr
            20                  25                  30

Gly Met Ser Trp Val Arg Gln Ala Pro Gly Lys Gly Leu Glu Leu Val
        35                  40                  45
```

```
Ala Asn Ile Asn Thr Asn Gly Gly Ser Thr Tyr Tyr Pro Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Thr Asn Asn Arg Tyr Asp Glu Asp Tyr Trp Gly Gln Gly Thr Leu Val
            100                 105                 110

Thr Val Ser Ser
        115

<210> SEQ ID NO 25
<211> LENGTH: 107
<212> TYPE: PRT
<213> ORGANISM: Artificial Sequence
<220> FEATURE:
<223> OTHER INFORMATION: amino acid sequence of the light-chain variable
      region of humanized anti-hTfR antibody No.2

<400> SEQUENCE: 25

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Ser Asn Asn
             20                  25                  30

Leu Gln Trp Tyr Gln Gln Lys Pro Asp Gln Ser Pro Lys Leu Leu Ile
        35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Leu Cys Gln Gln Ser Asn Ser Trp Pro Arg
                85                  90                  95

Thr Phe Gly Gln Gly Thr Lys Val Glu Ile Lys
            100                 105

<210> SEQ ID NO 26
<211> LENGTH: 120
<212> TYPE: PRT
<213> ORGANISM: Artificial Sequence
<220> FEATURE:
<223> OTHER INFORMATION: amino acid sequence of the heavy-chain variable
      region of humanized anti-hTfR antibody No.2

<400> SEQUENCE: 26

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Val Met His Trp Val Arg Gln Ala Pro Gly Gln Gly Leu Glu Trp Ile
        35                  40                  45

Gly Val Ile Ser Thr Tyr Tyr Gly His Gly Ser Tyr Asn Gln Arg Phe
 50                  55                  60

Lys Gly Arg Ala Thr Met Thr Val Asp Lys Ser Ile Ser Thr Ala Tyr
 65                  70                  75                  80

Met Glu Leu Val Arg Leu Arg Ser Asp Asp Thr Ala Val Tyr Tyr Cys
                85                  90                  95

Val Arg Gly Gly Tyr Gly Ser Ser Ser Leu Ala Gly Asn Phe Asp Val
            100                 105                 110
```

```
Trp Gly Gln Gly Thr Thr Val Thr
            115                 120

<210> SEQ ID NO 27
<211> LENGTH: 112
<212> TYPE: PRT
<213> ORGANISM: Artificial Sequence
<220> FEATURE:
<223> OTHER INFORMATION: amino acid sequence of the light-chain variable
      region of humanized anti-hTfR antibody No.3

<400> SEQUENCE: 27

Asp Ile Val Met Thr Gln Thr Pro Leu Ser Leu Ser Val Thr Pro Gly
1               5                   10                  15

Gln Pro Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

<210> SEQ ID NO 28
<211> LENGTH: 118
<212> TYPE: PRT
<213> ORGANISM: Artificial Sequence
<220> FEATURE:
<223> OTHER INFORMATION: amino acid sequence of the heavy-chain variable
      region of humanized anti-hTfR antibody No.3

<400> SEQUENCE: 28

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser
            115
```

AQUEOUS PHARMACEUTICAL COMPOSITION

This application is a national stage application of PCT/JP2018/033143 filed Sep. 7, 2018, the disclosure of which is incorporated by reference herein by reference in its entirety. This application claims priority to Japanese application 2017-172156 filed Sep. 7, 2017, the disclosure of which is incorporated herein in its entirety.

TECHNICAL FIELD

The present invention relates to an aqueous pharmaceutical composition, which is stable in storage in solution, of a drug containing as an active ingredient a protein in which an antibody and a lysosomal enzyme are linked, and more particularly, relates to an aqueous pharmaceutical composition containing sucrose and a nonionic surfactant as a stabilizing agent.

BACKGROUND OF THE INVENTION

Previously pharmaceuticals containing a protein as an active ingredient have been generally supplied as lyophilized preparations in consideration of storage stability of the protein. At present, many of pharmaceuticals are produced and sold in the form of aqueous pharmaceutical compositions, which contain as an active ingredient a lysosomal enzymes such as iduronate-2-sulfatase, α-galactosidase A, glucocerebrosidase, α-L-iduronidase, N-acetylgalactosamine-4-sulfatase, an antibody such as anti-human IL-6 receptor antibody and anti-human PD-1 antibody, or a physiologically active protein such as erythropoietin, darbepoetin, and growth hormones. Aqueous pharmaceutical compositions are more convenient than lyophilized formulations because they do not require for dissolving the drug before use.

Aqueous pharmaceutical compositions contain various additives to enhance the stability of a protein which is the main agent. As additives having an effect of enhancing the stability of a protein in an aqueous solution, for example, amino acids including histidine, methionine, arginine, and glycine, nonionic surfactants including polysorbate 80, and a buffer including a phosphate buffer are known. For example, in the case of an aqueous pharmaceutical composition of growth hormone, it is known that the stability of growth hormone is enhanced by adding histidine as a stabilizing agent (Patent Literature 1). In addition, in the case of an aqueous pharmaceutical composition of darbepoetin, it is known that the stability of darbepoetin is enhanced by adding methionine as a stabilizing agent (Patent Literature 2). Thus, the composition of the aqueous pharmaceutical composition differs from one aqueous pharmaceutical composition to another, and has been devised according to the properties of the protein as the main agent.

PRIOR ART LITERATURE

Patent Literature

[Patent Literature 1] Japanese Patent Publication No. 2000-508665

[Patent Literature 2] Japanese Patent Publication No. 2005-527470

SUMMARY OF THE INVENTION

Problem to be Solved by the Invention

The objective of the present invention is to provide an aqueous pharmaceutical composition, which is stable enough to be marketed, comprising sucrose and a nonionic surfactant as stabilizing agents, and as an active a protein in which an antibody and a lysosomal enzyme are linked.

Means for Solving the Problems

In a study directed to the above object, the present inventors have found that a protein in which an antibody and human iduronate-2-sulfatase, which is one of human lysosomal enzymes, are coupled is stable in an aqueous pharmaceutical composition containing sucrose and a nonionic surfactant, and have completed the present invention. That is, the present invention includes the following.

1. An aqueous pharmaceutical composition comprising a fusion protein of an antibody and a lysosomal enzyme as an active ingredient, wherein the concentration of the fusion protein is 0.5 to 20 mg/mL, the concentration of sodium chloride is 0.3 to 1.2 mg/mL, the concentration of sucrose is 50 to 100 mg/mL, the concentration of a nonionic surfactant is 0.15 to 3 mg/mL, the concentration of a buffer is 3 to 30 mM, and the pH is 5.0 to 7.5.
2. An aqueous pharmaceutical composition comprising a fusion protein of an antibody and a lysosomal enzyme as an active ingredient, wherein the concentration of the fusion protein is 1.0 to 10 mg/mL, the concentration of sodium chloride is 0.6 to 1.0 mg/mL, the concentration of sucrose is 55 to 95 mg/mL, the concentration of a nonionic surfactant is 0.15 to 1 mg/mL, the concentration of a buffer is 10 to 30 mM, and the pH is 5.5 to 7.0.
3. The aqueous pharmaceutical composition according to 1 or 2 above, wherein the concentration of the fusion protein is 2.0 to 10 mg/mL.
4. The aqueous pharmaceutical composition according to any one of 1 to 3 above, wherein the concentration of the sodium chloride is 0.7 to 0.9 mg/mL.
5. The aqueous pharmaceutical composition according to any one of 1 to 4 above, wherein the concentration of the sucrose is 60 to 90 mg/mL.
6. The aqueous pharmaceutical composition according to any one of 1 to 5 above, wherein the concentration of the nonionic surfactant is 0.3 to 0.8 mg/mL.
7. The aqueous pharmaceutical composition according to any one of 1 to 6 above, wherein the nonionic surfactant is polysorbate or poloxamer.
8. The aqueous pharmaceutical composition according to any one of 1 to 6 above, wherein the nonionic surfactant is selected from the group consisting of polysorbate 20, polysorbate 80, and polyoxyethylene (160) polyoxypropylene (30) glycol.
9. The aqueous pharmaceutical composition according to any one of 1 to 8 above, wherein the buffer is a phosphate buffer.
10. The aqueous pharmaceutical composition according to 9 above, wherein the phosphate buffer concentration is to 25 mM.
11. The aqueous pharmaceutical composition according to any one of 1 to 10 above, wherein the pH is 6.0 to 7.0.
12. The aqueous pharmaceutical composition according to any one of 1 to 10 above, wherein the pH is 6.2 to 6.8.
13. The aqueous pharmaceutical composition according to any one of 1 to 12 above, wherein the fusion protein is obtained by conjugating the human lysosomal enzyme to either the C-terminal side or N-terminal side of either the light chain or the heavy chain of the antibody by a peptide bond.

14. The aqueous pharmaceutical composition according to any one of 1 to 12 above, wherein the fusion protein is obtained by conjugating the human lysosomal enzyme to the C-terminal side of the heavy chain of the antibody by a peptide bond.

15. The aqueous pharmaceutical composition according to any one of 1 to 12 above, wherein the fusion protein is obtained by conjugating the human lysosomal enzyme to either the C-terminal side or N-terminal side of either the light chain or the heavy chain of the antibody via a peptide linker containing one or more amino acid residues.

16. The aqueous pharmaceutical composition according to any one of 1 to 12 above, wherein the fusion protein is obtained by conjugating the human lysosomal enzyme to the C-terminal side of the heavy chain of the antibody via a peptide linker containing one or more of amino acid residues.

17. The aqueous pharmaceutical composition according to 15 or 16 above, wherein the peptide linker has an amino acid sequence represented by Gly-Ser.

18. The aqueous pharmaceutical composition according to any one of 1 to 17 above, wherein the lysosomal enzyme is a human lysosomal enzyme.

19. The aqueous pharmaceutical composition according to any one of 1 to 18 above, wherein the lysosomal enzyme is selected from the group consisting of α-L-iduronidase, iduronate-2-sulfatase, glucocerebrosidase, β-galactosidase, GM2 activator, β-hexosaminidase A, β-hexosaminidase B, N-acetylglucosamine-1-phosphotransferase, α-mannosidase, β-mannosidase, galactosylceramidase, saposin C, arylsulfatase A, α-L-fucosidase, aspartylglucosaminidase, α-N-acetylgalactosaminidase, acid sphingomyelinase, α-galactosidase, β-glucuronidase, heparan-N-sulfatase, α-N-acetylglucosaminidase, acetyl-CoA:α-glucosaminide N-acetyltransferase, N-acetylglucosamine-6-sulfate sulfatase, acid ceramidase, amylo-1,6-glucosidase, sialidase, aspartylglucosaminidase, palmitoyl-protein thioesterase 1 (PPT-1), tripeptidyl-peptidase 1 (TPP-1), hyaluronidase-1, CLN1, and CLN2.

20. The aqueous pharmaceutical composition according to 18 above, wherein the human lysosomal enzyme is human iduronate-2-sulfatase.

21. The aqueous pharmaceutical composition according to any one of 1 to 20 above, wherein the antibody is a human antibody or a humanized antibody.

22. The aqueous pharmaceutical composition according to any one of claims 1 to 21, wherein the antibody recognizes a molecule present on the surface of a vascular endothelial cell as an antigen.

23. The aqueous pharmaceutical composition according to 22 above, wherein the vascular endothelial cell is a human vascular endothelial cell.

24. The aqueous pharmaceutical composition according to claim 22 or 23, wherein the vascular endothelial cell is a cerebrovascular endothelial cell.

25. The aqueous pharmaceutical composition according to claim 24, wherein the molecule present on the surface of the cerebrovascular endothelial cell is selected from the group consisting of transferrin receptor (TfR), insulin receptor, leptin receptor, lipoprotein receptor, IGF receptor, OATP-F, organic anion transporter, MCT-8, and monocarboxylic acid transporter.

26. The aqueous pharmaceutical composition according to claim 21, wherein the antibody is a humanized anti-human transferrin receptor (hTfR) antibody.

27. The aqueous pharmaceutical composition according to claim 21, wherein the antibody is the humanized anti-hTfR antibody, the human lysosomal enzyme is the human iduronate-2-sulfatase, the fusion protein is a fusion protein of the humanized anti-hTfR antibody and the human iduronate-2-sulfatase, and the fusion protein is selected from the group consisting of (a) to (c) below:
   (a) the fusion protein consisting of a light chain of the humanized anti-hTfR antibody having the amino acid sequence set forth as SEQ ID NO:2, and a heavy chain of the humanized anti-hTfR antibody having the amino acid sequence set forth as SEQ ID NO:8 and linked on the C-terminal side thereof and via a peptide linker to the human iduronate-2-sulfatase;
   (b) the fusion protein consisting of a light chain of a humanized anti-hTfR antibody having the amino acid sequence set forth as SEQ ID NO:4, and a heavy chain of the humanized anti-hTfR antibody having the amino acid sequence set forth as SEQ ID NO:9 and linked on the C-terminal side thereof and via a peptide linker to the human iduronate-2-sulfatase; and
   (c) the fusion protein consisting of a light chain of a humanized anti-hTfR antibody having the amino acid sequence set forth as SEQ ID NO:6, and a heavy chain of the humanized anti-hTfR antibody having the amino acid sequence set forth as SEQ ID NO:10 and linked on the C-terminal side thereof and via a peptide linker to the human iduronate-2-sulfatase.

28. The aqueous pharmaceutical composition according to claim 21, wherein the antibody is the humanized anti-hTfR antibody, the human lysosomal enzyme is the human iduronate-2-sulfatase, the fusion protein is a fusion protein of the humanized anti-hTfR antibody and the human iduronate-2-sulfatase, and the fusion protein is selected from the group consisting of (a) to (c) below:
   (a) the fusion protein, wherein the light chain of the humanized anti-hTfR antibody has the amino acid sequence set forth as SEQ ID NO:2, and the heavy chain of the humanized anti-hTfR antibody is linked, on the C-terminal side thereof and via a linker sequence Gly-Ser, to the human iduronate 2-sulfatase, and the whole linked heavy chain has the amino acid sequence set forth as SEQ ID NO:13,
   (b) the fusion protein, wherein the light chain of the humanized anti-hTfR antibody has the amino acid sequence set forth as SEQ ID NO:4, and the heavy chain of the humanized anti-hTfR antibody is linked, on the C-terminal side thereof and via a linker sequence Gly-Ser, to the human iduronate 2-sulfatase, and the whole linked heavy chain has the amino acid sequence set forth as SEQ ID NO:15; and
   (c) the fusion protein, wherein the light chain of the humanized anti-hTfR antibody has the amino acid sequence set forth as SEQ ID NO:6, and the heavy chain of the humanized anti-hTfR antibody is linked, on the C-terminal side thereof and via a linker sequence Gly-Ser, to the human iduronate 2-sulfatase, and the whole linked heavy chain has the amino acid sequence set forth as SEQ ID NO:17.

29. The aqueous pharmaceutical composition according to claim 21, wherein the antibody is the humanized anti-hTfR antibody, the human lysosomal enzyme is the human iduronate-2-sulfatase, the fusion protein is a fusion protein of the humanized anti-hTfR antibody and the human iduronate-2-sulfatase, and the fusion protein is selected from the group consisting of (a) to (c) below;
(a) the fusion protein consisting of a conjugate, in the conjugate the human iduronate-2-sulfatase is linked at the C-terminal side of the heavy chain via a linker sequence Gly-Ser, and the light chain, wherein the conjugate has the amino acid sequence set forth as SEQ ID NO:13 and the light chain has the amino acid sequence set forth as SEQ ID NO:2,
(b) the fusion protein consisting of a conjugate, in the conjugate the human iduronate-2-sulfatase is linked at the C-terminal side of the heavy chain via a linker sequence Gly-Ser, and the light chain, wherein the conjugate has the amino acid sequence set forth as SEQ ID NO:15 and the light chain has the amino acid sequence set forth as SEQ ID NO:4, and
(c) the fusion protein consisting of a conjugate, in the conjugate the human iduronate-2-sulfatase is linked at the C-terminal side of the heavy chain via a linker sequence Gly-Ser, and the light chain, wherein the conjugate has the amino acid sequence set forth as SEQ ID NO:17 and the light chain has the amino acid sequence set forth as SEQ ID NO:6.

Effect of the Invention

According to the present invention, a fusion protein in which an antibody and a lysosomal enzyme are linked to each other can be stabilized in an aqueous pharmaceutical composition to such an extent that the fusion protein can be marketed.

BRIEF DESCRIPTION OF THE DRAWINGS

FIG. 1-2 shows an enlarged view of FIG. 1-1 in the poloxamer 188 concentration range (0.25-5 mg/mL). The vertical axis represents the number of particles (/200 μL), and the horizontal axis represents the concentration of poloxamer 188 (mg/mL).

FIG. 2 shows the amount of polymers of I2S-anti-hTfR antibodies in aqueous pharmaceutical compositions after hours of shaking (black bars) and 24 hours (hatched bars). The vertical axis represents the amount of polymers (%), and the horizontal axis represents the concentration of the poloxamer 188 (mg/mL).

DESCRIPTION OF THE EMBODIMENTS

Figure 1:
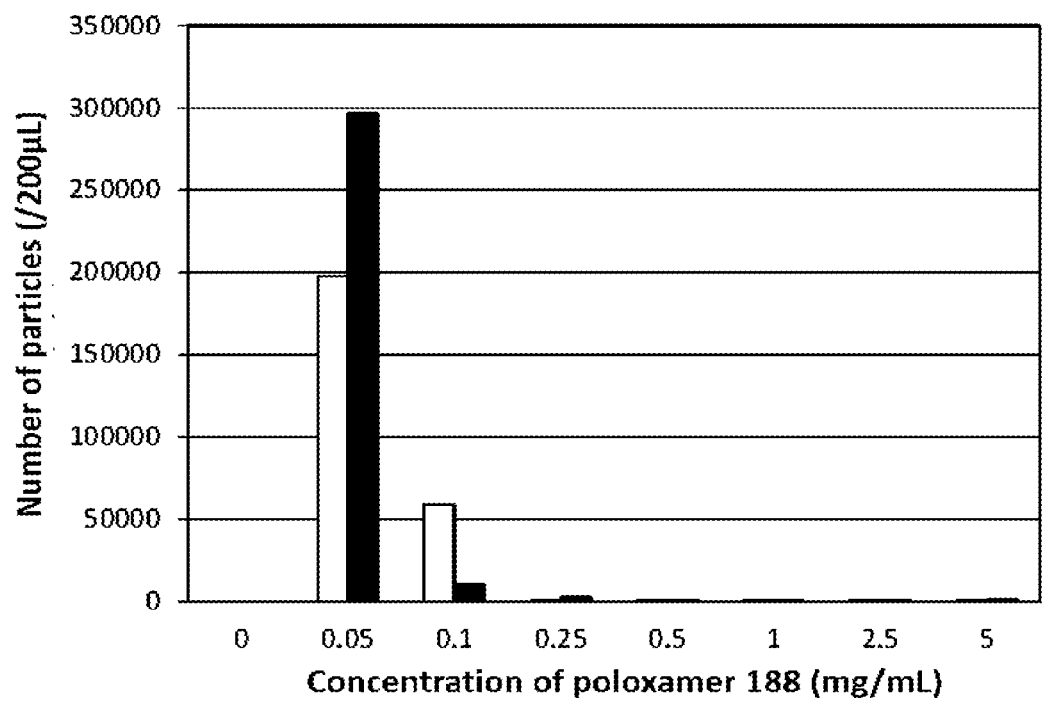
FIG. 1-1 shows the measured number of particles per unit liquid volume (200 μL) in an aqueous pharmaceutical composition after 6 hours of shaking (white bar) and 24 hours (black bar). The vertical axis represents the number of particles (/200 μL), and the horizontal axis represents the concentration of poloxamer 188 (mg/mL).
Figures 1, 2:
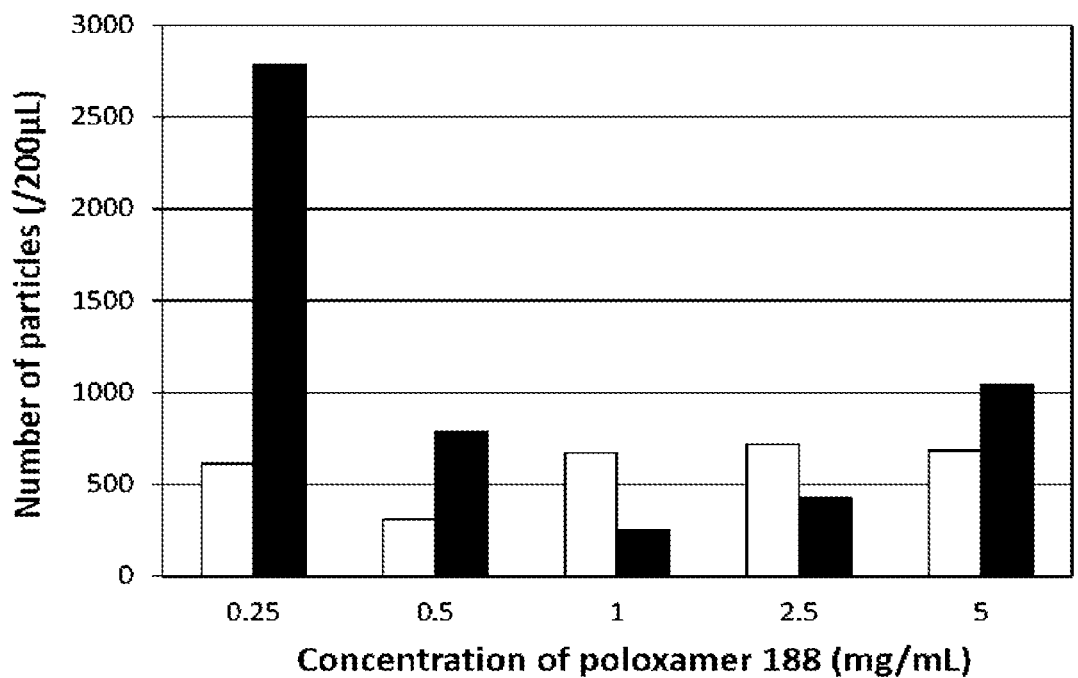
Figure 2:
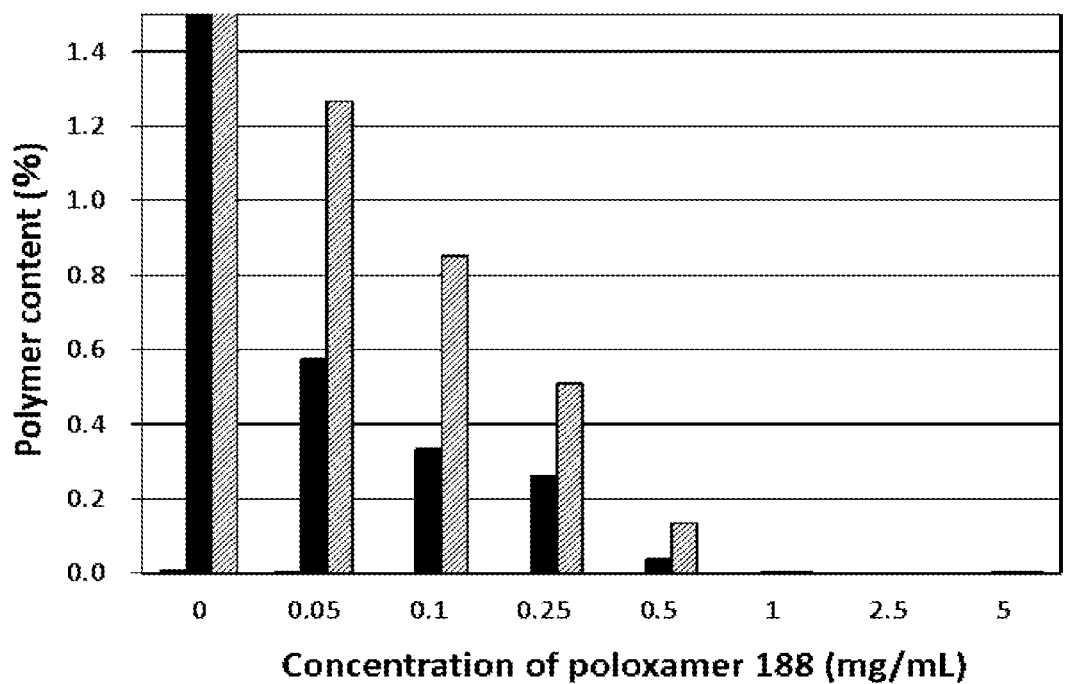

The present invention relates to an aqueous pharmaceutical composition, which is stable in storage in solution, of a drug containing as an active ingredient a protein in which an antibody and a lysosomal enzyme are linked. Here, the antibody to be bound to the lysosomal enzyme is preferably a human antibody or a humanized antibody, but there is no particular limitation as to the animal species of the antibody or the like as long as it has a property of binding specifically to the antigen. For example, the antibody may be an antibody of a non-human mammal, and a chimeric antibody of a human antibody and an antibody of a non-human mammal.

The term "human antibody" refers to the antibody whose entire protein is encoded by a gene originating from human. However, the antibody encoded by a gene obtained by introducing a mutation into an original human gene for a purpose of enhancing expression efficacy of the gene, for example, without modifying the original amino acid sequence is also included in "human antibody".

The term "human antibody" also includes an antibody which is produced by combining two or more genes encoding human antibodies and replacing certain part of a human antibody with part of another human antibody. A human antibody includes three complementarity determining regions (CDRs) in the light chain of the immunoglobulin and three complementarity determining regions (CDRs) in the heavy chain of the immunoglobulin. The three CDRs in the light chain of the immunoglobulin are called, from the N-terminal side, CDR1, CDR2 and CDR3, respectively. The three CDRs in the heavy chain of the immunoglobulin are also called, from the N-terminal side, CDR1, CDR2 and CDR3, respectively. The term "human antibody" also includes a human antibody produced by replacing a CDR of a human antibody with a CDR of another human antibody to modify such properties as the antigen specificity and the affinity of the original human antibodies, etc.

In the present invention, the term "human antibody" also includes an antibody which is produced through modification of the gene of the original human antibody by introducing a mutation, such as substitution, deletion, addition, to the amino acid sequence of the original antibody. When replacing one or more amino acid residues of the amino acid sequence of the original antibody with other amino acid residues, the number of amino acid replaced may preferably be 1 to 20, more preferably 1 to 5, still more preferably 1 to 3. When deleting one or more amino acid residues of the amino acid sequence of the original antibody, the number of amino acid residues deleted may preferably be 1 to 20, more preferably 1 to 5, and still more preferably 1 to 3. An antibody produced by a combined mutation of these substitution and deletion of amino acid residues is also a "human antibody". In some cases, one or more amino acids, preferably 1 to 20, more preferably 1 to 5, and still more preferably 1 to 3 amino acid residues may be added inside the amino acid sequence of the original antibody or on its N- or C-terminus. An antibody produced by a combination of two of these mutations, i.e. addition, substitution, and deletion of amino acid residues, is also a "human antibody". The amino acid sequence of such a mutated antibody has an identity of preferably not lower than 80%, more preferably not lower than 85%, still more preferably not lower than 90%, still more preferably not lower than 95%, and even more preferably not lower than 98%, to the amino acid sequence of the original antibody. Thus, in the present invention, the term "gene originating from human" includes not only the unmutated gene originating from human but also a gene produced by modifying it.

In the present invention, the term "humanized antibody" refers to an antibody in which part of the amino acid sequence of its variable region (e.g., especially the whole or part of its CDRs) originates from a non-human mammal while the rest originates from human. An example of humanized antibody is an antibody produced by replacing the three complementarity determining regions (CDRs) of the light chain of the immunoglobulin and the three complementarity determining regions (CDRs) of the heavy chain of the immunoglobulin constituting a human antibody, with CDRs from a non-human mammal. As far as it originates from a non-human mammal, there is no particular limitation as to the biological species from which those CDRs originate that are grafted into a proper position of the human antibody, though preferred are mouse, rat, rabbit, horse or non-human primate, for example mouse.

A detailed explanation will be given below regarding the case where the antibody is a humanized antibody or human antibody. In human antibody light chain, there are λ and κ chains. The light chain constituting the antibody may either be λ and κ chain. And in heavy chain of human or humanized antibody, there are γ, m, α, σ, and ε chains, which correspond to IgG, IgM, IgA, IgD and IgE, respectively. Though the heavy chain constituting the antibody may be any of γ, m, α, σ, and ε chains, preferred is a γ chain. Further, in γ chain of antibody heavy chain, there are γ1, γ2, γ3 and γ4 chains, which correspond to IgG1, IgG2, IgG3 and IgG4, respectively. Where the heavy chain constituting the antibody is a γ chain, though the γ chain may be any of γ1, γ2, γ3 and γ4 chains, preferred is a γ1 or γ4 chain. In the case where the antibody is a humanized antibody or human antibody and IgG, the antibody light chain may either be λ chain or κ chain, and though the antibody heavy chain may either be γ1, γ2, γ3 and γ4 chains, preferred is a γ1 or γ4 chain. For example, a preferable embodiment of the antibody includes an antibody whose light chain is a λ chain and heavy chain is a γ1 chain.

In the present invention, the term "chimeric antibody" refers to an antibody produced by connecting fragments of two or more different antibodies originating from two or more different species.

A chimeric antibody between a human antibody and a non-human mammalian antibody is an antibody provided by replacing part of a human antibody with part of a non-human mammalian antibody. As explained below, an antibody is made of an Fc region, a Fab region and a hinge region. A specific example of such chimeric antibodies is a chimeric antibody whose Fc region originates from a human antibody while its Fab region originates from a non-human mammalian antibody. The hinge region either originates from a human antibody or from a non-human mammalian antibody. On the contrary, the term chimeric antibody also includes one whose Fc region originates from a non-human mammalian antibody while its Fab region originates from a human antibody. In such a case also, the hinge region either originates from a human antibody or from a non-human mammalian antibody.

An antibody can be viewed as composed of a variable region and a constant region. Additional examples of chimeric antibodies include an antibody in which the heavy chain constant region ($C_H$) and the light chain constant region ($C_L$) both originate from a human antibody while the heavy chain variable region ($V_H$) and the light chain variable region ($V_L$) both originate from an antibody of a non-human mammal, and conversely, an antibody in which the heavy chain constant region ($C_H$) and the light chain constant region ($C_L$) both originate from an antibody of a non-human mammal, while the heavy chain variable region ($V_H$) and the light chain variable region ($V_L$) both originate from a human antibody. In these, there is no particular limitation as to the biological species of the non-human mammal, as far as it is a non-human mammal, though preferred are mouse, rat, rabbit, horse or non-human primate, and mouse, more preferably mouse.

A chimeric antibody between a human antibody and a mouse antibody is designated in particular "human/mouse chimeric antibody". Examples of human/mouse chimeric antibodies include a chimeric antibody in which the Fc region originates from a human antibody while the Fab region originates from a mouse antibody, and conversely, a chimeric antibody whose Fc region originates from mouse antibody, while its Fab region originates from a human antibody. A hinge region either originates from a human antibody or a mouse antibody. Additional specific examples of human/mouse chimeric antibodies include those whose heavy chain constant region ($C_H$) and light chain constant region ($C_L$) originate from a human antibody while its heavy chain variable region ($V_H$) and light chain variable region (VL) originate from a mouse antibody, and conversely, those whose heavy chain constant region ($C_H$) and light chain constant region ($C_L$) originate from a mouse antibody while its heavy chain variable region ($V_H$) and light chain variable region (VL) originate from a human antibody.

Originally, an antibody is of the basic structure having four polypeptide chains in total consisting of two immunoglobulin light chains and two immunoglobulin heavy chains. However, in the present invention the term "antibody" refers, besides an antibody having this basic structure, also to:

(1) one consisting of two polypeptide chains in total, i.e. a single immunoglobulin light chain and a single immunoglobulin heavy chain, and also, as explained later, (2) a single-chain antibody consisting of an immunoglobulin light chain which is linked, on the C-terminal side thereof, to a linker sequence which in turn is linked, on the C-terminal side thereof, to an immunoglobulin heavy chain, (3) single-chain antibodies consisting of an immunoglobulin heavy chain which is linked, on the C-terminal side thereof, to a linker sequence which in turn is linked, on the C-terminal side thereof, to an immunoglobulin light chain, and (4) one consisting of a Fab region, i.e., a structure left behind by removal of the Fc region from an antibody having the basic structure, as the original meaning, and one consisting of the Fab region and the whole or part of the hinge region (including Fab, F(ab'), and F(ab')$_2$) also are included in the term "antibody" in the present invention. Furthermore, scFv in which the variable region of the light chain and the variable region of the heavy chain are linked via a linker sequence to form a single chain antibody is also included in the antibody of the present invention.

In the present invention, the term "single-chain antibody" refers to a protein in which an amino acid sequence comprising the whole or part of an immunoglobulin light chain variable region linked, on the C-terminal side thereof, to a linker sequence, which in turn is linked, on the C-terminal side thereof, to the amino acid sequence of the whole or part of an immunoglobulin heavy chain variable region, and having an ability to specifically bind a certain antigen. For example, those described in (2) and (3) are included in "single-chain antibody". Further, a protein in which an amino acid sequence comprising the whole or part of an immunoglobulin heavy chain variable region is linked, on the C-terminal side thereof, to a linker sequence, which in turn is further linked, on the C-terminal side thereof, to the amino acid sequence of the whole or part of an immunoglobulin light chain variable region, and which has an ability to specifically bind to a certain antigen, is also included in the term "single-chain antibody" in the present invention. In a single-chain antibody in which an immunoglobulin heavy chain is linked, on the C-terminal side thereof and via a linker sequence, to an immunoglobulin light chain, the immunoglobulin heavy chain generally lacks the Fc region. An immunoglobulin light chain variable region has three complementarity determining regions (CDRs) which participate in determining the antigen specificity of an antibody. Likewise, an immunoglobulin heavy chain variable region also has three CDRs. Those CDRs are the primary regions that determine the antigen specificity of an antibody. Therefore, a single-chain antibody preferably contains all the three CDRs of the immunoglobulin heavy chain and all the three CDRs of the immunoglobulin light chain. However, it is also possible to provide a single-chain antibody in which one or more of those CDRs are deleted, insofar as the antigen-specific affinity of the antibody is retained.

In a single-chain antibody, the linker sequence placed between the light chain and the heavy chain of the immunoglobulin is preferably a peptide chain consisting of preferably 2 to 50, more preferably 8 to 50, still more preferably 10 to 30, even more preferably 12 to 18, or 15 to 25, for example 15 or 25 amino acid residues. While there is no particular limitation as to the specific amino acid sequence of such a linker sequence insofar as the anti-hTfR antibody comprising the both chains linked thereby retains the affinity to hTfR, it is preferably made of glycine only, or of glycine and serine. For example, there are the amino acid sequence Gly-Ser, the amino acid sequence of Gly-Gly-Ser, the amino acid sequence of Gly-Gly-Gly, the amino acid sequence of Gly-Gly-Gly-Gly-Ser (SEQ ID NO:19), the amino acid sequence of Gly-Gly-Gly-Gly-Gly-Ser (SEQ ID NO:20), the amino acid sequence of Ser-Gly-Gly-Gly-Gly-Gly (SEQ ID NO:21), or a sequence which includes a sequence corresponding to 2 to 10 or 2 to 5 of any of those amino acid sequences consecutively linked. For example, in linking the amino acid sequence of the entire immunoglobulin heavy chain variable region on the C-terminal side thereof and via a linker sequence, to immunoglobulin light chain variable region to produce ScFV a preferable linker sequence comprises a linker sequence consisting of a total of 15 amino acid residues corresponding to three of the amino acid sequence of Gly-Gly-Gly-Gly-Ser (SEQ ID NO:19) consecutively linked.

In the present invention, the antigen specifically recognized by the antibody is, for example, a molecule present on the surface of vascular endothelial cells (surface antigen). Examples of such surface antigens include transferrin receptor (TfR), insulin receptor, leptin receptor, lipoprotein receptor, IGF receptor, organic anion transporters such as OATP-F, monocarboxylic acid transporters such as MCT-8, Fc receptors, and the like, but are not limited to these.

Among the surface antigens described above, organic anion transporters such as transferrin receptor (TfR), insulin receptor, leptin receptor, lipoprotein receptor, IGF receptor, OATP-F and the like, monocarboxylic acid transporter such as MCT-8 Porter is present on the surface of brain capillary endothelial cells forming the blood brain barrier (Blood Brain Barrier). Antibodies capable of recognizing these antigens can bind to brain capillary endothelial cells (cerebral vascular endothelial cells) via antigens. And antibodies bound to brain capillary endothelial cells can cross the blood brain barrier and reach the central nervous system. Therefore, by conjugating (binding) the protein of interest to such an antibody, it is possible to reach the central nervous system. Protein of interest may be a protein having a function to exert a drug effect in the central nervous system. For example, lysosomal enzymes that are deficient or dysfunctional in lysosomal disease patients with central nervous system disorders are mentioned as proteins of interest. Such a lysosomal enzyme cannot reach the central nervous system as it is and does not show a drug effect against a central nervous system disorder of a patient, but by allowing it to bind with these antibodies, it can pass through the blood brain barrier As a result, the central nervous system disorder found in lysosomal disease patients can be improved.

In the present invention, the term "human transferrin receptor" or "hTfR" refers to a membrane protein having the amino acid sequence set forth as SEQ ID NO:22. The anti-hTfR antibody of the present invention is, in one of its embodiments, that which binds also to the region from the cysteine residue at the position 89th from the N-terminus to the phenylalanine at the C-terminus in the amino acid sequence set forth as SEQ ID NO:22 (i.e., the extracellular region of the monkey TfR), though it is not limited to this embodiment.

A method for preparing an antibody is described below, an antibody against hTfR taken as an example. For preparation of an antibody to hTfR, there is known a general method according to which a recombinant human transferrin receptor (rhTfR) is produced using cells which have an introduced expression vector having an incorporated hTfR gene, and then animals such as mice are immunized with this rhTfR. By collecting those cells which produce antibodies to hTfR from the immunized animals and fusing them with myeloma cells, hybridoma cells can be obtained having an ability to produce the anti-hTfR antibody.

Further, cells producing an antibody to hTfR can also be obtained by collecting immunocompetent cells from an animal such as mouse, and immunizing them with rhTfR by in vitro immunization. In conducting immunization by vitro immunization, there is no particular limitation as to the animal species from which the immunocompetent cells are derived, though preferred are mouse, rat, rabbit, guinea pig, dog, cat, horse, and primates including human, and more preferred are mouse, rat and human, and still more preferably mouse and human. As mouse immunocompetent cells, spleen cells prepared from mouse spleen may be used, for example. As human immunocompetent cells, such cells can be used as prepared from a human tissue such as peripheral blood, bone marrow, and spleen. By immunizing human immunocompetent cells according to in vitro immunization, a human antibody to hTfR can be obtained.

In the present invention, there is no particular limitation as to the human lysosomal enzyme to be linked to the anti-hTfR antibody. As such lysosomal enzymes, included are α-L-iduronidase, iduronate-2-sulfatase, glucocerebrosidase, β-galactosidase, GM2 activator protein, β-hexosaminidase A, β-hexosaminidase B, N-acetylglucosamine-1-phosphotransferase, α-mannosidase, β-mannosidase, galactosylceramidase, saposin C, arylsulfatase A, α-L-fucosidase, aspartylglucosaminidase, α-N-acetylgalactosaminidase, acidic sphingomyelinase, α-galactosidase, β-glucuronidase, heparan N-sulfatase, α-N-acetylglucosaminidase, acetyl CoA:α-glucosaminide N-acetyltransferase, N-acetylglucosamine-6-sulfate sulfatase, acid ceramidase, amylo-1,6-glucosidase, sialidase, aspartylglucosaminidase (PPT1), tripeptidyl-peptidase 1 (TPP-1), hyaluronidase 1, CLN1, and CLN2, and the like.

When the antibody specifically recognizes a molecule present on the surface of the vascular endothelial cell surface antigen), the human lysosomal enzyme linked to the antibody can be used as a therapeutic agent for central nervous system disorders, i.e. α-L-iduronidase as a therapeutic agent for central nervous system disorders in Hurler syndrome or Hurler-Scheie syndrome; iduronate-2-sulfatase as a therapeutic agent for central nervous system disorders in Hunter syndrome; glucocerebrosidase as a therapeutic agent for central nervous system disorders in Gaucher's disease; β-galactosidase as a therapeutic agent for central nervous system disorders in GM1 gangliosidosis Types 1 to 3; GM2 activator protein as a therapeutic agent for central nervous system disorders in GM2-gangliosidosis, AB variant; β-hexosaminidase A as a therapeutic agent for central nervous system disorders in Sandhoffs disease and Tay-Sachs disease; β-hexosaminidase B as a therapeutic agent for central nervous system disorders in Sandhoffs disease; Nacetylglucosamine-1-phosphotransferase as a therapeutic agent for central nervous system disorders in I-cell disease; α-mannosidase as a therapeutic agent for central nervous system disorders in α-mannosidosis; β-mannosidase as a therapeutic agent for central nervous system disorders in β-mannosidosis; galactosylceramidase as a therapeutic agent for central nervous system disorders in Krabbe disease; saposin C as a therapeutic agent for central nervous system disorders in Gaucher's disease-like storage disease; arylsulfatase A as a therapeutic agent for central nervous system disorders in metachromatic white matter degeneration (metachromatic leukodystrophy); α-L-fucosidase as a therapeutic agent for central nervous system disorders in fucosidosis; aspartylglucosaminidase as a therapeutic agent for central nervous system disorders in aspartylglucosaminuria; α-N-acetylgalactosaminidase as a therapeutic agent for central nervous system disorders in Schindler disease and Kawasaki disease; acidic sphingomyelinase as a therapeutic agent for central nervous system disorders in Niemann-Pick disease; α-galactosidase as a therapeutic agent for central nervous system disorders in Fabry disease; β-glucuronidase as a therapeutic agent for central nervous system disorders in Sly syndrome; heparan N-sulfatase, α-N-acetylglucosaminidase, acetyl CoA:α-glucosaminide N-acetyltransferase and N-acetylglucosamine-6-sulfate sulfatase as therapeutic agents for central nervous system disorders in Sanfilippo syndrome; acid ceramidase as a therapeutic agent for central nervous system disorders in Farber disease; amylo-1,6-glucosidase as a therapeutic agent for central nervous system disorders in Cori's disease (Forbes-Cori's disease); sialidase as a therapeutic agent for central nervous system disorders in sialidase deficiency; aspartylglucosaminidase as a therapeutic agent for central nervous system disorders in aspartylglucosaminuria; palmitoyl protein thioesterase 1 (PPT-1) as a therapeutic agent for central nervous system disorders in neuronal ceroid lipofuscinosis or Santavuori-Haltia disease; tripeptidyl-peptidase 1 (TPP-1) as a therapeutic agent for central nervous system disorders in neuronal ceroid lipofuscinosis or Jansky-Bielschowsky disease; hyaluronidase 1 as a therapeutic agent for central nervous system disorders in hyaluronidase deficiency; CLN1 and CLN2 as therapeutic agents for central nervous system disorders in Batten disease. In particular, the anti-hTfR antibody of the present invention, after passing through the blood-brain barrier, reaches the brain parenchyma and the hippocampus neuron-like cells of the cerebrum, and Purkinje cells of the cerebellum, and is expected further to reach neuron-like cells of the striatum of the cerebrum and the neuron-like cells of the substantia nigra of the mesencephalon. Therefore, the anti-hTfR antibody can be fused with proteins which need to exhibit their functions in those tissues or cells to strength the pharmacological effects of the proteins. Medical applications of it, however, are not limited thereto.

In the case where the antibody specifically recognizes a molecule present on the surface of vascular endothelial cells (surface antigen), lysosomal enzymes to be preferably linked to the antibody include human iduronate-2-sulfatase (hI2S). HI2S is one of lysosome enzyme having an activity for hydrolyzing sulfate bonds present in glycosaminoglycan (GAG) molecules such as heparan sulfate and dermatan sulfate. Hunter syndrome is a genetic disorder in which this enzyme is congenitally deleted. In the patients of Hunter syndrome, heparan sulfate and dermatan sulfate accumulate in the tissues, resulting in various symptoms such as corneal opacity, mental development delay, and so on. However, in the mild cases, mental developmental delay may not be observed. Therefore, since the fusion protein between the antibody and hI2S can degrade GAG accumulated in brain tissues by passing through BBB, it can be used as a therapeutic agent for central nervous system disorders by administered to a patient with Hunter syndrome showing mental developmental delay.

In the present invention, the term "human I2S" or "hI2S" refers to hI2S particularly having the same amino acid sequence as wild type hI2S. The wild type hI2S has an amino acid sequence consisting of 525 amino acid residues set forth as SEQ ID NO: 5. However, not limited to this, a hI2S containing a mutation such as substitution, deletion, addition and so on added to the amino acid sequence of the wild type hI2S is also included in hI2S, as long as it has I2S activity. When amino acid residues of the amino acid sequence of hI2S are substituted with other amino acid residues, the number of amino acid residues to be substituted is preferably 1 to 10, more preferably 1 to 5, still more preferably 1 to 3, and still more preferably 1 to 2. When amino acid residues in the amino acid sequence of hI2S are deleted, the number of amino acid residues to be deleted is preferably 1 to 10, more preferably 1 to 5, still more preferably 1 to 3, and still more preferably 1 to 2. A combined mutation of these substitution and deletion of amino acid residues can also be carried out. When adding one or more amino acid residues to the hI2S, they may be added inside, or on the N-terminal side or C-terminal side thereof, and the number of amino acid residues added is preferably 1 to 10, more preferably 1 to 5, still more preferably 1 to 3, and even more preferably 1 or 2. A combined mutation of at least two of these substitution, deletion, and addition of amino acid residues can also be carried out. The amino acid sequence of such a mutated hI2S has an identity of preferably not lower than 80%, more preferably not lower than 85%, still more preferably not lower than 90%, and still more preferably not lower than 95%, to the amino acid sequence of the original hI2S.

The statement that hI2S has the I2S activity herein means that the hI2S fused to an antibody has an activity not lower than 3% of the activity that the natural-type hI2S intrinsically has. However, the activity is preferably not lower than 10%, more preferably not lower than 20%, still more preferably not lower than 50%, even more preferably not lower than 80% of the activity that the natural-type hI2S intrinsically has. The same also applies when the I2S has one or more of mutations. The antibody is, for example, an anti-hTfR antibody.

In the present invention, the term "fusion protein" refers to a substance obtained by binding an antibody and a human lysosomal enzyme directly, or via a non-peptide linker or a peptide linker. Methods for conjugating antibodies and human lysosomal enzymes are described in detail below.

For conjugating an antibody to a lysosomal enzyme, a method is available to bind them together via a non-peptide linker or a peptide linker. As non-peptide linkers, there can be used biotin-streptavidin, polyethylene glycol, polypropylene glycol, copolymer of ethylene glycol and propylene glycol, polyoxyethylated polyol, polyvinyl alcohol, polysaccharides, dextran, polyvinyl ether, biodegradable polymer, polymerized lipid, chitins, and hyaluronic acid, or derivatives thereof, or combinations thereof. A peptide linker is a peptide chain consisting of 1 to 50 amino acid residues linked by peptide bonds or a derivative thereof, whose N-terminus and C-terminus are to be covalently bonded either to the antibody or the lysosomal enzyme, respectively, to bind the antibody to such a c lysosomal enzyme.

When biotin-streptavidin is used as the non-peptide linker, the antibody and a human lysosomal enzyme may be bound to each other via binding between biotin and streptavidin, where the antibody is bound to the biotin, and the human lysosomal enzyme is bound to the streptavidin. Conversely, the antibody and a human lysosomal enzyme may be bound to each other via binding between biotin and streptavidin, where the antibody is bound to the streptavidin, and the human lysosomal enzyme is bound to the biotin. Biotin and streptavidin can be coupled to proteins by well-known techniques.

In particular, a conjugate which is formed by conjugating the antibody of the present invention to human lysosomal enzyme via PEG as a non-peptide linker, is designated "anti-antibody-PEG-human lysosomal enzyme". An anti-antibody-PEG-human lysosomal enzyme can be prepared by first binding the antibody to PEG to form antibody-PEG, and then binding the antibody-PEG to the human lysosomal enzyme. Alternatively, an anti-antibody-PEG-human lysosomal enzyme can be prepared by first binding the human lysosomal enzyme to PEG to form "human lysosomal enzyme-PEG", and then binding the "human lysosomal enzyme-PEG" to the antibody. In order to bind PEG to the antibody and the human lysosomal enzyme, a PEG is employed which is modified with such functional groups as carbonate, carbonylimidazole, active ester of carboxylic acid, azlactone, cyclic imide thione, isocyanate, isothiocyanate, imidate, aldehyde or the like. Such functional groups introduced to PEG react mainly with amino groups in the antibody and the human lysosomal enzyme to covalently bind PEG to the antibody and the human lysosomal enzyme. Though there is no particular limitation as to the molecular weight and the configuration of PEG employed here, its mean molecular weight (MW) is as follows: preferably MW=500 to 60000, more preferably MW=500 to 20000. For example, such PEG whose mean molecular weight is about 300, about 500, about 1000, about 2000, about 4000, about 10000, about 20000, and the like. PEG is preferably used as a non-peptide linker.

For example, "antibody-PEG" can be prepared by mixing the antibody with a polyethylene glycol having aldehyde groups as functional groups (ALD-PEG-ALD) so that the molar ratio of ALD-PEG-ALD to the antibody is 11, 12.5, 15, 110, 120 and the like, and then adding to the mixture a reducing agent such as NaCNBH3 to let a reaction take place. Then, by reacting "anti-hTfR antibody-PEG" with a human lysosomal enzyme in the presence of a reducing agent such as NaCNBH3, "antibody-PEG-protein" is obtained. On the contrary, it is also possible to obtain "antibody-PEG-protein" by first binding a human lysosomal enzyme to ALD-PEG-ALD to prepare "human lysosomal enzyme-PEG", and then binding the "human lysosomal enzyme-PEG" to the antibody.

The antibody and a human lysosomal enzyme can also be bound together through peptide bonds by linking the antibody heavy chain or light chain, on the C-terminal side or the N-terminal side thereof, either via a linker sequence or directly, to the N-terminus or the C-terminus of the human lysosomal enzyme, respectively. Thus the fusion protein between the antibody and a human lysosomal enzyme can be obtained by incorporating into an expression vector for eukaryotic cell such as mammalian cells and yeast a DNA fragment in which a cDNA encoding the human lysosomal enzyme is placed in-frame directly, or via a DNA fragment encoding a linker sequence, on the 3'-end or 5'-end side of a cDNA encoding the heavy chain or light chain of the antibody, and culturing the cells into which the above expression vector has been introduced. Where the DNA fragment encoding a human lysosomal enzyme is linked to the heavy chain, an expression vector in which a cDNA fragment encoding the antibody light chain is also introduced into the same host cells, whereas if DNA fragment encoding a human lysosomal enzyme is linked to the light chain, an expression vector in which a cDNA fragment encoding the antibody heavy chain is also incorporated into the same host cells. In the case where the antibody is a single-chain antibody, the fusion protein comprising the antibody and a human lysosomal enzyme combined can be obtained by incorporating, into an expression vector for eukaryotic cells such as mammalian and yeast, a DNA fragment which is formed by linking the cDNA encoding a human lysosomal enzyme, on the 5'-end side or on the 3'-end side thereof, directly or via a DNA fragment encoding a linker sequence, to the cDNA encoding the single-chain antibody, and allowing the fusion protein be expressed in those cells into which the expression vector has been introduced.

In a fusion protein of the type in which a human lysosomal enzyme is linked to the antibody light chain on the C-terminal side thereof, the antibody comprises an amino acid sequence including the whole or part of the light chain variable region and an amino acid sequence including the whole or part of the heavy chain variable region, and the human lysosomal enzyme is linked to the light chain of this antibody on the C-terminal side thereof. Here, the antibody light chain and a human lysosomal enzyme may be linked together, directly or via a linker.

In a fusion protein of the type in which a human lysosomal enzyme is linked to the antibody heavy chain on the C-terminal side thereof, the antibody comprises an amino acid sequence including the whole or part of the light chain variable region and an amino acid sequence including the whole or part of the heavy chain variable region, and the human lysosomal enzyme is linked to the heavy chain of this antibody on the C-terminal side thereof. Here, the antibody heavy chain and a human lysosomal enzyme may be linked together, directly or via a linker.

In a fusion protein of the type in which a human lysosomal enzyme is linked to the antibody light chain on the N-terminal side thereof, the antibody comprises an amino acid sequence including the whole or part of the light chain variable region and an amino acid sequence including the whole or part of the heavy chain variable region, and the human lysosomal enzyme is linked to the light chain of this antibody on the N-terminal side thereof. Here, the antibody light chain and a human lysosomal enzyme may be linked together, directly or via a linker.

In a fusion protein of the type in which a human lysosomal enzyme is linked to the antibody heavy chain on the N-terminal side thereof, the antibody comprises an amino acid sequence including the whole or part of the light chain variable region and an amino acid sequence including the whole or part of the heavy chain variable region, and the human lysosomal enzyme is linked to the heavy chain of this antibody on the N-terminal side thereof. Here, the antibody heavy chain and a human lysosomal enzyme may be linked together, directly or via a linker.

In the above, when the linker sequence is placed between the antibody and a human lysosomal enzyme, the linker sequence may be a peptide chain consisting preferably of 1 to 50, more preferably of 1 to 17, still more preferably of 1 to 10, even more preferably of 1 to 5 amino acid residues, and in accordance with the human lysosomal enzyme to be linked to the anti-hTfR antibody, the number of amino acid residues of the linker sequence may be adjusted to 1, 2, 3, 1 to 17, 1 to 10, 10 to 40, 20 to 34, 23 to 31, 25 to 29, etc., as desired. Though there is no particular limitation as to amino acid sequence of the linker sequence insofar as the antibody linked by it retains the affinity to hTfR and a human lysosomal enzyme linked by the linker sequence also exhibits the protein's own physiological activity under a physiological condition, the linker may preferably be composed of glycine and serine. Examples of such linkers include one consisting of a single amino acid either glycine or serine, the amino acid sequence of Gly-Ser, the amino acid sequence of Gly-Gly-Ser, the amino acid sequence of Gly-Gly-Gly-Gly-Ser (SEQ ID NO:19), the amino acid sequence of Gly-Gly-Gly-Gly-Gly-Ser (SEQ ID NO:20), the amino acid sequence of Ser-Gly-Gly-Gly-Gly-Gly (SEQ ID NO:21), or a sequence which includes 1 to 10 or 2 to 5 of any of those amino acid sequences consecutively linked. They have sequences consisting of 1 to 50, 2 to 17, 2 to 10, 10 to 40, 20 to 34, 23 to 31, or 25 to 29 amino acid residues. For example, those comprising the amino acid sequence of Gly-Ser may preferably be used as linker sequences. Same can be applied when the antibody is a single strand antibody.

Besides, in the present invention, when a peptide chain includes a plurality of linker sequences, each of those linker sequences is designated, from the N-terminal side, the first linker sequence, the second linker sequence, and so on, for convenience.

Preferred embodiments of the antibody, that antibody is a humanized antibody and an anti-human transferrin receptor antibody, include the following (x) to (z) below, (X) the light chain comprises the amino acid sequence set forth as SEQ ID NO: 2, and the heavy chain comprises the amino acid sequence set forth as SEQ ID NO: 8;

(Y) the light chain comprises the amino acid sequence set forth as SEQ ID NO: 4, and the heavy chain comprises the amino acid sequence set forth as SEQ ID NO: 9;

(Z) the light chain comprises the amino acid sequence set forth as SEQ ID NO: 6, and the heavy chain comprises the amino acid sequence set forth as SEQ ID NO: 10. Here, (x), (y) and (z) correspond to a humanized anti-hTfR antibody No. 1, a humanized anti-hTfR antibody No. 2, and a humanized anti-hTfR antibody No. 3, respectively, that antibodies are described in the examples.

However, preferred embodiments of the antibody are not limited to the (x) to (z) above, when the antibody is a humanized antibody and an anti-human transferrin receptor antibody. For example, the antibody can be used in the present invention, whose amino acid sequence of the light chain has an identity not lower than 80% to the amino acid sequence of each one of light chain in the above (x) to (z), and whose amino acid sequence of the heavy chain has an identity not lower than 80% to the amino acid sequence of each one of heavy chain in the above (x) to (z) insofar as that antibody has affinity for hTfR. For example, the antibody can be used in the present invention, whose amino acid sequence of the light chain has an identity not lower than 85% to the amino acid sequence of each one of light chain in the above (x) to (z), and whose amino acid sequence of the heavy chain has an identity not lower than 85% to the amino acid sequence of each one of heavy chain in the above (x) to (z) insofar as that antibody has affinity for hTfR. For example, the antibody can be used in the present invention, whose amino acid sequence of the light chain has an identity not lower than 90% to the amino acid sequence of each one of light chain in the above (x) to (z), and whose amino acid sequence of the heavy chain has an identity not lower than 90% to the amino acid sequence of each one of heavy chain in the above (x) to (z) insofar as that antibody has affinity for hTfR. For example, the antibody can be used in the present invention, whose amino acid sequence of the light chain has an identity not lower than 95% to the amino acid sequence of each one of light chain in the above (x) to (z), and whose amino acid sequence of the heavy chain has an identity not lower than 95% to the amino acid sequence of each one of heavy chain in the above (x) to (z) insofar as that antibody has affinity for hTfR.

In addition, as long as the antibody has affinity for hTfR, an antibody in which 1 to 10 amino acid residues constituting the amino acid sequence of each light chain in (x) to (z) above are substituted, deleted, or added, and 1 to 10 amino acid residues constituting the amino acid sequence of each heavy chain in (x) to (z) above are substituted, deleted, or added can also be used as the antibody of the present invention. In addition, as long as the antibody has affinity for hTfR, an antibody in which 1 to 5 amino acid residues constituting the amino acid sequence of each light chain in (x) to (z) above are substituted, deleted, or added, and 1 to 5 amino acid residues constituting the amino acid sequence of each heavy chain in (x) to (z) above are substituted, deleted, or added can also be used as the antibody of the present invention. Furthermore, as long as the antibody has affinity for hTfR, an antibody in which 1 to 3 amino acid residues constituting the amino acid sequence of each light chain in (x) to (z) above are substituted, deleted, or added, and 1 to 3 amino acid residues constituting the amino acid sequence of each heavy chain in (x) to (z) above are substituted, deleted, or added can also be used as the antibody of the present invention.

In the preferred embodiment (x) of the above antibody, in the amino acid sequence of the light chain set forth as SEQ ID NO:2, the amino acid sequence set forth as SEQ ID NO:23 is a variable region, and in the amino acid sequence of the heavy chain set forth as SEQ ID NO:8, the amino acid sequence set forth as SEQ ID NO:24 is a variable region. Also, in the preferred embodiment (y) of the above antibody, in the amino acid sequence of the light chain set forth as SEQ ID NO:4, the amino acid sequence set forth as SEQ ID NO:25 is a variable region, and in the amino acid sequence of the heavy chain set forth as SEQ ID NO:9, the amino acid sequence set forth as SEQ ID NO:26 is a variable region. Further, in the preferred embodiment (z) of the above antibody, in the amino acid sequence of the light chain set forth as SEQ ID NO:6, the amino acid sequence set forth as SEQ ID NO:27 is a variable region, and in the amino acid sequence of the heavy chain set forth as SEQ ID NO:10, the amino acid sequence set forth as SEQ ID NO:28 is a variable region. In the preferred embodiments (x) to (z) of these antibodies, substitutions, deletions or additions into the amino acid sequence constituting the amino acid sequence of the heavy or/and light chains are introduced in particular into these variable regions. However, the variable region may be an amino acid sequence excluding 1 to 10 amino acid residues, an amino acid sequence excluding 1 to 5 amino acid residues, or an amino acid sequence excluding 1 to 3 amino acid residues on the C-terminal side of the amino acid sequence set forth as the variable region of the light chain above. The variable region may be an amino acid sequence including 1 to 10 amino acid residues, an amino acid sequence including 1 to 5 amino acid residues, or an amino acid sequence including 1 to 3 amino acid residues, following the amino acid sequence set forth as the variable region of the light chain above. The variable region may be an amino acid sequence excluding 1 to 10 amino acid residues, an amino acid sequence excluding 1 to 5 amino acid residues, or an amino acid sequence excluding 1 to 3 amino acid residues on the C-terminal side of the amino acid sequence set forth as the variable region of the heavy chain above. The variable region may be an amino acid sequence including 1 to 10 amino acid residues, an amino acid sequence including 1 to 5 amino acid residues, or an amino acid sequence including 1 to 3 amino acid residues, following the amino acid sequence set forth as the variable region of the heavy chain above.

In the present invention, the identity between the amino acid sequence of the original protein (including the antibody) and the amino acid sequence of the protein to which the mutation has been added can be easily calculated using a well-known homology calculation algorithm. For example, as such algorithms, BLAST (Altschul S F. J Mol. Biol. 215. 403-10, (1990), Pearson and Lipman similarity search methods (Proc) Natl. Acad. Sci. USA. 85. Local Homology Algorithms of 2444 (1988), Smith and Waterman (Adv) Appl. Math. 2. Include 482-9 (1981)

As a preferable embodiment of a fusion protein of an antibody and a human lysosomal enzyme, a fusion protein of a humanized anti-human transferrin receptor antibody (humanized anti-hTfR antibody) and human iduronate-2-sulfatase (hI2S) can be exemplified. In this fusion protein, the hI2S may be fused to either the heavy or the light chain constituting the humanized anti-hTfR antibody, as long as the affinity for the human transferrin receptor and the enzymatic activity of the human lysosomal enzyme can be retained. The hI2S may be fused to either the N-terminal side or the C-terminal side of the heavy chain when the hI2S is attached to the heavy chain, and the hI2S may be fused to either the N-terminal side or the C-terminal side of the light chain when the hI2S is attached to the light chain.

As a preferable embodiment of the fusion protein of the humanized anti-hTfR antibody and the hI2S, there is a fusion protein in which human iduronate-2-sulfatase is conjugated to the C-terminal side of the heavy chain of the humanized anti-hTfR antibody. Examples of preferable fusion proteins include those shown in (1) to (3) below:

(1) a fusion protein consisting of the light chain of humanized anti-hTfR antibody having the amino acid sequence set forth as SEQ ID NO:2, and the heavy chain of humanized anti-hTfR antibody having the amino acid sequence set forth as SEQ ID NO:8 and linked, on the C-terminus thereof via a linker sequence, to human iduronate-2-sulfatase, (2) a fusion protein consisting of the light chain of humanized anti-hTfR antibody having the amino acid sequence set forth as SEQ ID NO:4, and the heavy chain of humanized anti-hTfR antibody having the amino acid sequence set forth as SEQ ID NO:9 and linked, on the C-terminus thereof via a linker sequence, to human iduronate-2-sulfatase, and (3) a fusion protein consisting of the light chain of humanized anti-hTfR antibody having the amino acid sequence set forth as SEQ ID NO:6, and the heavy chain of humanized anti-hTfR antibody having the amino acid sequence set forth as SEQ ID NO:10 and linked, on the C-terminus thereof via a linker sequence, to human iduronate-2-sulfatase.

In these fusion proteins (1) to (3), the human iduronate-2-sulfatase preferably has the amino acid sequence set forth as SEQ ID NO:1, and the linker sequence preferably has the amino acid sequence represented by (Gly-Ser). These fusion proteins usually comprise two light chains and two heavy chains linked to human iduronate-2-sulfatase.

In addition, examples of preferable fusion protein of the humanized anti-hTfR antibody and hI2S include those shown in (1) to (3) below:

(1) a fusion protein comprising a light chain of the humanized anti-hTfR antibody having the amino acid sequence set forth as SEQ ID NO: 2, and a heavy chain of the humanized anti-hTfR antibody linked, on the C-terminal side thereof and via a linker sequence of Gly-Ser, to the human iduronate-2-sulfatase, and having the amino acid sequence set forth as SEQ ID NO:13 as the whole linked heavy chain, (2) a fusion protein comprising a light chain of the humanized anti-hTfR antibody having the amino acid sequence set forth as SEQ ID NO: 4, and a heavy chain of the humanized anti-hTfR antibody linked, on the C-terminal side thereof and via a linker sequence of Gly-Ser, to the human iduronate-2-sulfatase, and having the amino acid sequence set forth as SEQ ID NO:15 as the whole linked heavy chain, (3) a fusion protein comprising a light chain of the humanized anti-hTfR antibody having the amino acid sequence set forth as SEQ ID NO: 6, and a heavy chain of the humanized anti-hTfR antibody linked, on the C-terminal side thereof and via a linker sequence of Gly-Ser, to the human iduronate-2-sulfatase, and having the amino acid sequence set forth as SEQ ID NO:17 as the whole linked heavy chain.

These fusion proteins usually comprise two light chains and two heavy chains linked to human iduronate-2-sulfatase.

Further, examples of preferable fusion protein of the humanized anti-hTfR antibody and hI2S include those shown in (1) to (3) below:
(1) the fusion protein comprising the conjugate composed of human iduronate 2-sulfatase linked via a linker sequence Gly-Ser to the heavy chain on the C-terminal side thereof; and the light chain, wherein the amino acid sequence of the conjugate is set forth as SEQ ID NO13, and the amino acid sequence of the light chain is set forth as SEQ ID NO:2,
(2) the fusion protein comprising the conjugate composed of human iduronate 2-sulfatase linked via a linker sequence Gly-Ser to the heavy chain on the C-terminal side thereof; and the light chain, wherein the amino acid sequence of the conjugate is set forth as SEQ ID NO15, and the amino acid sequence of the light chain is set forth as SEQ ID NO:4, and
(3) the fusion protein comprising the conjugate composed of human iduronate 2-sulfatase linked via a linker sequence Gly-Ser to the heavy chain on the C-terminal side thereof; and the light chain, wherein the amino acid sequence of the conjugate is set forth as SEQ ID NO:17, and the amino acid sequence of the light chain is set forth as SEQ ID NO:6.

These fusion proteins are usually comprises two light chains and two heavy chains, the two heavy chains linked to human iduronate-2-sulfatase.

In one embodiment of the present invention, the aqueous pharmaceutical composition comprises a fusion protein of an antibody and a human lysosomal enzyme as an active ingredient, primarily sodium chloride as an isotonic agent, primarily sucrose and a nonionic surfactant as a stabilizing agent, and a buffering agent as a pH adjusting agent.

The concentration of the fusion protein of the antibody and the human lysosomal enzyme contained in 0.5 to 20 mg/mL, more preferably 1.0 to 10 mg/mL, even more preferably 2.0 to 10 mg/mL, still more preferably 2.0 to 6.0 mg/mL, for example 2.5 mg/mL and 5.0 mg/mL.

The concentration of sodium chloride contained in the aqueous pharmaceutical composition is preferably 0.3 to 1.2 mg/mL, more preferably 0.5 to 1.0 mg/mL, even more preferably 0.6 to 1.0 mg/mL, still more preferably 0.7 to 0.9 mg/mL, for example 0.8 mg/mL.

The concentration of sucrose contained in the aqueous pharmaceutical composition is preferably from 50 to 100 mg/mL, more preferably from 55 to 95 mg/mL, even more preferably from 60 to 90 mg/mL, still more preferably from 70 to 80 mg/mL, for example 75 mg/mL.

As the nonionic surfactant contained in the aqueous pharmaceutical composition, a polysorbate, a poloxamer, or the like can be used alone or in combination thereof. Polysorbate 20 and polysorbate 80 are particularly suitable as a polysorbate, and poloxamer 188 (polyoxyethylene (160) polyoxypropylene (30) glycol) is particularly suitable as a poloxamer. The concentration of the nonionic surfactant contained in the aqueous pharmaceutical composition is preferably from 0.15 to 3 mg/mL, more preferably from 0.15 to 1 mg/mL, even more preferably from 0.2 to 0.8 mg/mL, still more preferably from 0.3 to 0.8 mg/mL, for example, 0.325 mg/mL and 0.65 mg/mL.

The buffering agent contained in the aqueous pharmaceutical composition is not particularly limited as long as it is pharmaceutically acceptable, but a phosphate buffering agent is preferable. When a phosphate buffer is used as the buffer, the concentration of the phosphate buffer contained in the aqueous pharmaceutical composition is preferably from 3 to 30 mM, more preferably from 10 to 30 mM, even more preferably from 15 to 25 mM, for example 20 mM. The pH of the aqueous pharmaceutical composition adjusted by the buffer is preferably 5.5 to 7.5, more preferably 5.5 to 7.0, even more preferably 6.0 to 7.0, still more preferably 6.2 to 6.8, for example 6.5. The osmotic pressure ratio of the aqueous pharmaceutical composition to the physiological saline is adjusted to 0.9 to 1.1.

Suitable compositions of the aqueous pharmaceutical composition of the present invention include:
(A) a composition in which the concentration of fusion protein of an antibody and a human lysosomal enzyme is from 0.5 to 20 mg/mL, the concentration of sodium chloride is from 0.3 to 1.2 mg/mL, the concentration of sucrose is from 50 to 100 mg/mL, the concentration of nonionic surfactant is from 0.15 to 1 mg/mL, the concentration of buffer is from 3 to 30 mM, and pH is from 5.0 to 7.5,
(B) a composition in which the concentration of fusion protein of an antibody and a human lysosomal enzyme is from 1.0 to 10 mg/mL, the concentration of sodium chloride is from 0.6 to 1.0 mg/mL, the concentration of sucrose is from 55 to 95 mg/mL, the concentration of nonionic surfactant is from 0.15 to 1 mg/mL, the concentration of buffer is from 10 to 30 mM, and pH is from 5.5 to 7.0.

In the aqueous pharmaceutical compositions shown in (A) and (B) above, the fusion protein of the antibody and the human lysosomal enzyme is, for example, a fusion protein of the humanized anti-hTfR antibody and hI2S. Preferable embodiments of such a fusion protein of a humanized anti-hTfR antibody and hI2S include:
(1) a fusion protein in which the light chain of the humanized anti-hTfR antibody has the amino acid sequence set forth as SEQ ID NO:2, the heavy chain of the humanized anti-hTfR antibody has the amino acid sequence set forth as SEQ ID NO:8, and human iduronate-2-sulfatase is linked to the C-terminal side of the heavy chain via a linker sequence,
(2) a fusion protein in which the light chain of the humanized anti-hTfR antibody has the amino acid sequence set forth as SEQ ID NO:4, the heavy chain of the humanized anti-hTfR antibody has the amino acid sequence set forth as SEQ ID NO:9, and human iduronate-2-sulfatase is linked to the C-terminal side of the heavy chain via a linker sequence,
(3) a fusion protein in which the light chain of the humanized anti-hTfR antibody has the amino acid sequence set forth as SEQ ID NO:6, the heavy chain of the humanized anti-hTfR antibody has the amino acid sequence set forth as SEQ ID NO: 10, and human iduronate-2-sulfatase is linked to the C-terminal side of the heavy chain via a linker sequence.

In the above-mentioned fusion proteins (1) to (3), the human iduronate-2-sulfatase preferably has the amino acid sequence set forth as SEQ ID NO:1, and the linker sequence preferably has the amino acid sequence set forth as (Gly-Ser). These fusion proteins are usually comprise two light chains and two heavy chains linked to human iduronate-2-sulfatase.

Further, preferable embodiments of a fusion protein of a humanized anti-hTfR antibody and hI2S in aqueous pharmaceutical compositions shown in (A) and (B) above include:
(1) a fusion protein comprising a light chain of the humanized anti-hTfR antibody having the amino acid sequence set forth as SEQ ID NO: 2, and a heavy chain of the humanized anti-hTfR antibody linked, on the C-terminal side thereof and via a linker sequence Gly-Ser, to the human iduronate-2-sulfatase, and having the amino acid sequence set forth as SEQ ID NO:13 as the whole, (2) a fusion protein comprising a light chain of the humanized anti-hTfR antibody having the amino acid sequence set forth as SEQ ID NO: 4, and a heavy chain of the humanized anti-hTfR antibody linked, on the C-terminal side thereof and via a linker sequence Gly-Ser, to the human iduronate-2-sulfatase, and having the amino acid sequence set forth as SEQ ID NO:15 as the whole, and (3) a fusion protein comprising a light chain of the humanized anti-hTfR antibody having the amino acid sequence set forth as SEQ ID NO: 6, and a heavy chain of the humanized anti-hTfR antibody linked, on the C-terminal side thereof and via a linker sequence Gly-Ser, to the human iduronate-2-sulfatase, and having the amino acid sequence set forth as SEQ ID NO:17 as the whole.

Further, preferable embodiments of a fusion protein of a humanized anti-hTfR antibody and hI2S in aqueous pharmaceutical compositions shown in (A) and (B) above include: anti-hTfR (1) the fusion protein comprising the conjugate composed of human iduronate 2-sulfatase linked via a linker sequence Gly-Ser to the heavy chain on the C-terminal side thereof; and the light chain, wherein the amino acid sequence of the conjugate is set forth as SEQ ID NO13, and the amino acid sequence of the light chain is set forth as SEQ ID NO:2, (2) the fusion protein comprising the conjugate composed of human iduronate 2-sulfatase linked via a linker sequence Gly-Ser to the heavy chain on the C-terminal side thereof; and the light chain, wherein the amino acid sequence of the conjugate is set forth as SEQ ID NO15, and the amino acid sequence of the light chain is set forth as SEQ ID NO:4, and (3) the fusion protein comprising the conjugate composed of human iduronate 2-sulfatase linked via a linker sequence Gly-Ser to the heavy chain on the C-terminal side thereof; and the light chain, wherein the amino acid sequence of the conjugate is set forth as SEQ ID NO:17, and the amino acid sequence of the light chain is set forth as SEQ ID NO:6.

These fusion proteins are usually comprises two light chains and two heavy chains, the two heavy chains linked to human iduronate-2-sulfatase.

In the aqueous pharmaceutical compositions represented by (A) or (B) above, the preferred concentration of the fusion protein of the humanized anti-hTfR antibody and hI2S is 0.5 to 20 mg/mL, 1.0 to mg/mL, 2.0 to 10 mg/mL, or 2.0 to 6.0 mg/mL, and adjusted as appropriate to 2.5 mg/mL, 5.0 mg/mL, or the like.

In the aqueous pharmaceutical composition represented by (A) or (B) above, the preferred concentration of sodium chloride is 0.3 to 1.2 mg/mL, 0.5 to 1.0 mg/mL, 0.6 to 1.0 mg/mL, or 0.7 to 0.9 mg/mL, for example, 0.8 mg/mL.

In the aqueous pharmaceutical composition represented by (A) or (B) above, the preferred concentration of sucrose is 50 to 100 mg/mL, 55 to 95 mg/mL, 60 to 90 mg/mL, or 70 to 80 mg/mL, for example, 75 mg/mL.

In the aqueous pharmaceutical composition represented by (A) or (B) above, a polysorbate, a poloxamer, or the like can be used alone or in combination as the nonionic surfactant. Polysorbate 20 and polysorbate 80 are particularly suitable as a polysorbate, and poloxamer 188 (polyoxyethylene (160) polyoxypropylene (30) glycol) is particularly suitable as a poloxamer. The concentration is preferably 0.15 to 3 mg/mL, more preferably 0.15 to 1 mg/mL, even more preferably 0.2 to 0.8 mg/mL, still more preferably 0.3 to 0.8 mg/mL, for example 0.325 mg/mL and 0.65 mg/mL.

The buffering agent used in the aqueous pharmaceutical composition represented by (A) or (B) above is not particularly limited as long as it is pharmaceutically acceptable, but a phosphate buffering agent is preferable. When a phosphate buffer is used as the buffer, its concentration is preferably from 3 to 30 mM, more preferably from 10 to 30 mM, even more preferably from 15 to 25 mM, for example 20 mM. The pH of the aqueous pharmaceutical composition adjusted by the buffer is preferably 5.5 to 7.5, more preferably 5.5 to 7.0, even more preferably 6.0 to 7.0, still more preferably 6.2 to 6.8, for example 6.5. The osmotic pressure ratio of the aqueous pharmaceutical composition to the physiological saline is adjusted to 0.9 to 1.1.

When the fusion protein of the antibody and the human lysosomal enzyme is a fusion protein of the humanized anti-hTfR antibody and the hI2S, examples of suitable compositions of the aqueous pharmaceutical composition include those in which the concentration of the fusion protein is 5 mg/mL, the concentration of sodium chloride is 0.8 mg/mL, the concentration of sucrose is 75 mg/mL, the concentration of the nonionic surfactant is 0.65 mg/mL, and the concentration of the phosphate buffer is 20 mM. In this aqueous pharmaceutical composition, the pH is preferably adjusted from 6.0 to 7.0, more preferably from 6.2 to 6.8, and the osmotic pressure ratio to saline is adjusted from 0.9 to 1.1. The nonionic surfactant is preferably polysorbate or poloxamer, polysorbate 20 or polysorbate 80 as polysorbate, and poloxamer 188 (polyoxyethylene (160) polyoxypropylene (30) glycol) as poloxamer. Among these, poloxamer 188 can be suitably used as a nonionic surfactant.

When the fusion protein of the antibody and the human lysosomal enzyme is a fusion protein of the humanized anti-hTfR antibody and the hI2S, examples of suitable compositions of the aqueous pharmaceutical composition further include those in which the concentration of the fusion protein is 2.5 mg/mL, the concentration of sodium chloride is 0.8 mg/mL, the concentration of sucrose is 75 mg/mL, the concentration of nonionic surfactant is 0.325 mg/mL, and the concentration of phosphate buffer is 20 mM. In this aqueous pharmaceutical composition, the pH is preferably adjusted from 6.0 to 7.0, more preferably from 6.2 to 6.8, and the osmotic pressure ratio to saline is adjusted from 0.9 to 1.1. The nonionic surfactant is preferably polysorbate or poloxamer, polysorbate 20 or polysorbate 80 is suitably used as the polysorbate, and poloxamer 188 (polyoxyethylene (160) polyoxypropylene (30) glycol) is suitably used as the poloxamer, and poloxamer 188 is particularly suitable.

The aqueous pharmaceutical composition of the present invention containing a fusion protein of an antibody and a human lysosomal enzyme as an active ingredient can be administered intravenously, intramuscularly, intraperitoneally or subcutaneously as an injection. The aqueous pharmaceutical composition of the present invention may be in the form of a vial or may be supplied as a prefilled formulation that is prefilled into a syringe.

EXAMPLES

While the present invention will be described in further detail below referring to examples, it is not intended that the present invention be limited to the examples.

Example 1

Construction of the Vector for Expression of a hI2S-Humanized Anti-hTfR Antibody-Fusion Protein An expression vector for hI2S-humanized anti-hTfR antibody fusion protein was constructed using genes encoding three types of humanized anti-hTfR antibodies (Nos. 1 to 3). The antibody No. 1 comprises a light chain having the amino acid sequence set forth as SEQ ID NO:2 and a heavy chain having the amino acid sequence set forth as SEQ ID NO:8, the antibody No. 2 comprises a light chain having the amino acid sequence set forth as SEQ ID NO:4 and a heavy chain having the amino acid sequence set forth as SEQ ID NO:9, the antibody No. 3 comprises a light chain having the amino acid sequence set forth as SEQ ID NO:6 and a heavy chain having the amino acid sequence set forth as SEQ ID NO:10, respectively.

A pEF/myc/nuc vector (Invitrogen Inc.) was digested with KpnI and NcoI to cut out the region containing the EF-1α promoter and its first intron, and the region was blunt-ended with T4 DNA polymerase. A pCI-neo (Invitrogen Inc.) was digested with BglII and EcoRI to cut out the region containing the enhancer/promoter and intron of CMV, and then the region was blunt-ended with T4 DNA polymerase. The above region containing the EF-1α promoter and its first intron was inserted into this to construct a pE-neo vector. The pE-neo vector was digested with SfiI and BstXI and a region of approximately 1 kbp containing the neomycin resistance gene was cut out. Amplification of hygromycin gene was carried out by PCR reaction using primers Hyg-SfiI5' (SEQ ID NO:11) and Hyg-BstX3' (SEQ ID NO:12) and using pcDNA 3.1/Hygro(+) (Invitrogen Inc.) as a template. The amplified hygromycin gene was digested with SfiI and BstXI and inserted into the pE-neo vector from which the above neomycin resistance gene has been cut out. The obtained vector was used as a pE-hygr vector.

A DNA fragment (SEQ ID NO:3) containing the gene encoding the full length of the light chain of the humanized anti-hTfR antibody No. 1 having the amino acid sequence set forth as SEQ ID NO:2 was synthesized. A MluI sequence was introduced on the 5' side of this DNA fragment and a NotI sequence on the 3' side thereof. This DNA fragment was digested with MluI and NotI and incorporated between MluI and NotI of the pE-neo vector. The obtained vector was designated pE-hygr (LC1) which is a vector for expressing the light chain of humanized anti-hTfR antibody No. 1.

A DNA fragment (SEQ ID NO:5) containing a gene encoding the full length of the light chain of humanized anti-hTfR antibody No. 2 having the amino acid sequence set forth as SEQ ID NO:4 was synthesized. The MluI sequence was introduced on the 5' side of this DNA fragment and the NotI sequence on the 3' side thereof. This DNA fragment was digested with MluI and NotI and incorporated between MluI and NotI of the pE-neo vector. The resulting vector was designated pE-hygr (LC2) which is a vector for expressing the light chain of humanized anti-hTfR antibody No. 2.

A DNA fragment (SEQ ID NO:7) containing a gene encoding the full length of the light chain of humanized anti-hTfR antibody No. 3 having the amino acid sequence set forth as SEQ ID NO:6 was synthesized. The MluI sequence was introduced on the 5' side of this DNA fragment and the NotI sequence on the 3' side thereof. This DNA fragment was digested with MluI and NotI and incorporated between MluI and NotI of the pE-neo vector. The obtained vector was defined as pE-hygr (LC3) which is a vector for expressing the light chain of humanized anti-hTfR antibody No. 3.

A DNA fragment was artificially synthesized, having a nucleotide sequence set forth as SEQ ID NO: 14 containing a gene encoding a protein in which hI2S having an amino acid sequence set forth as SEQ ID NO:1 is linked to the C-terminal side of the heavy chain of the humanized anti-hTfR antibody No. 1 having an amino acid sequence set forth as SEQ ID NO:8 via a linker having an amino acid sequence set forth as (Gly-Ser). This DNA fragment encodes a protein having the amino acid sequence set forth as SEQ ID NO:13, in which a heavy chain of humanized anti-hTfR antibody No. 1 binds to hI2S. This DNA fragment was digested with MluI and NotI and inserted between MluI and Not of the pE-neo vector to construct pE-neo (HC-I2S-1).

A DNA fragment was artificially synthesized, having a nucleotide sequence set forth as SEQ ID NO:16 containing a gene encoding a protein in which hI2S having an amino acid sequence set forth as SEQ ID NO:1 is linked to the C-terminal side of the heavy chain of the humanized anti-hTfR antibody No. 2 having an amino acid sequence set forth as SEQ ID NO:9 via a linker having an amino acid sequence set forth as (Gly-Ser). This DNA fragment encodes a protein having the amino acid sequence set forth as SEQ ID NO:15, in which a heavy chain of humanized anti-hTfR antibody No. 2 binds to hI2S. This DNA fragment was digested with MluI and NotI and inserted between MluI and NotI of the pE-neo vector to construct pE-neo (HC-I2S-2).

A DNA fragment was artificially synthesized, having a nucleotide sequence set forth as SEQ ID NO:18 containing a gene encoding a protein in which hI2S having an amino acid sequence set forth as SEQ ID NO:1 is linked to the C-terminal side of the heavy chain of the humanized anti-hTfR antibody No. 3 having an amino acid sequence set forth as SEQ ID NO:10 via a linker having an amino acid sequence set forth as (Gly-Ser). This DNA fragment encodes a protein having the amino acid sequence set forth as SEQ ID NO:17, in which a heavy chain of humanized anti-hTfR antibody No. 3 binds to hI2S. This DNA fragment was digested with MluI and NotI and inserted between MluI and NotI of the pE-neo vector to construct pE-neo (HC-I2S-3).

Example 2

Preparation of a High Expression Cell Lines of hI2S-Humanized Anti-hTfR Antibody Fusion Proteins CHO cells (CHO-K1 obtained from American Type Culture Collection) were transformed with combinations of pE-hygr (LC1) and pE-neo (HC-I2S-1) constructed in Example 1, pE-hygr (LC2) and pE-neo (HC-I2S-2) constructed in Example 1 and pE-hygr (LC3) and pE-neo (HC-I2S-3) constructed in Example 1, respectively, using the GenePulser (Bio-Rad Inc.). Transformation of cells was in brief carried out by the following method.

$5 \times 10^5$ of CHO-K1 cells were seeded in a 3.5 cm culture dish to which CD OptiCHO™ medium (Thermo Fisher Scientific Inc.) was added and cultured overnight at 37° C. under 5% $CO_2$. After the culture, the cells were suspended in Opti-MEM™ I medium (Thermo Fisher Scientific Inc.) to a density of $5 \times 10^6$ cells/mL. 100 µL of the cell suspension was collected, and thereto 5 µL each of the pE-hygr (LC1) and pE-neo (HC-I2S-1) plasmid DNA solutions both having been diluted to 100 µg/mL with CD OptiCHO™ medium was added. Electroporation was performed using GenePulser (Bio-Rad Inc.) to introduce the plasmids into the cells. After overnight culture under the condition of 37° C., 5% $CO_2$, the cells were selectively cultured in CD OptiCHO™ medium supplemented with 0.5 mg/mL of hygromycin and 0.8 mg/mL of G418. For the combination of pE-hygr (LC2) and pE-neo (HC-I2S-2) and the combination of pE-hygr (LC3) and pE-neo (HC-I2S-3), the transformations of the cells were conducted by the same method.

Then, the cells selected above through the selection culture were seeded on 96-well plates so that not more than one cell might be seeded per well by limiting dilution. The cells then were cultured for about 10 days so that monoclonal colonies formed. Respective culture supernatants of the wells in which monoclonal colony formed were collected, the amount of the humanized antibody contained in culture supernatants was determined by ELISA method, and the hI2S-humanized anti-hTfR antibody fusion protein high-expressing cell lines were selected.

The ELISA above was conducted as follows in general. To each well of 96-well microtiter plates (Nunc Inc.) was added 100 µL of a goat anti-human IgG polyclonal antibody solution diluted with 0.05 M sodium bicarbonate buffer (pH 9.6) to 4 µg/mL, and the plate was left to stand for at least one hour at room temperature so as to allow the antibody to be adsorbed by the plates. Then, after each well was washed three times with a phosphate-buffered saline (pH 7.4) supplemented with 0.05% Tween20 (PBS-T), 200 µL of Starting Block (PBS) Blocking Buffer (Thermo Fisher Scientific Inc.) was added to each well, and the plates were left to stand for 30 minutes at room temperature. After each well was washed with PBS-T three times, the culture supernatant or the human IgG reference standard product which had been diluted with a phosphate buffer saline (pH 7.4) supplemented with 0.5% BSA and 0.05% Tween20 (PBS-BT) to appropriate concentrations, was added to each well, in the amount of 100 µL, and the plates were left to stand for at least one hour at room temperature. After the plates were washed three times with PBS-T, 100 µL of HRP-labeled anti-human IgG polyclonal antibody solution which had been diluted with PBS-BT, was added to each well, and the plates were left to stand for at least one hour at room temperature. After the wells were washed three times with PBS-T, citrate-phosphate buffer (pH 5.0) containing 0.4 mg/mL o-phenylenediamine was added to each well, in the amount of 100 µL, and the wells were left to stand for 8 to 20 minutes at room temperature. Then, 1 mol/L sulfuric acid was added to each well in the amount of 100 µL to terminate the reaction, and the absorbance for each well was measured at 490 nm using a 96-well plate reader. The cells corresponding to the wells which exhibited the higher measurements were regarded as a high-expressing cell line for hI2S-humanized anti-hTfR antibody fusion protein.

A high-expressing cell line of a hI2S-humanized anti-hTfR antibody fusion protein obtained by transformation with combination of pE-hygr (LC1) and pE-neo (HC-I2S-1) was designated as a hI2S-anti-hTfR antibody expressing strain 1. The fusion protein of hI2S and humanized anti-hTfR antibody expressed by this cell line was designated as I2S-anti-hTfR antibody 1.

A high-expressing cell line of a hI2S-humanized anti-hTfR antibody fusion protein obtained by transformation with combination of pE-hygr (LC2) and pE-neo (HC-I2S-2) was designated as a hI2S-anti-hTfR antibody expressing strain 2. The fusion protein of hI2S and humanized anti-hTfR antibody expressed by this cell line was designated as I2S-anti-hTfR antibody 2.

A high-expressing cell line of a hI2S-humanized anti-hTfR antibody fusion protein obtained by transformation with combination of pE-hygr (LC3) and pE-neo (HC-I2S-3) was designated as a hI2S-anti-hTfR antibody expressing strain 3. The fusion protein of hI2S and humanized anti-hTfR antibody expressed by this cell line was designated as I2S-anti-hTfR antibody 3.

Example 3

Culture of hI2S-Anti-hTfR Antibody Expressing Strain

The hI2S-anti-hTfR antibodies were produced by the method described below. The hI2S-anti-hTfR antibody expressing strain 3 obtained in Example 2 was suspended in about 200 L of serum-free medium (EX-CELL Advanced CHO Fed-batch Medium, Sigma Aldrich Inc.) containing 4 mM L-alanyl-L-glutamine, 100 µmol/L hypoxanthine and 16 µmol/L thymidine to the density of about $2 \times 10^5$ cells/mL. 140 L of this cell suspension was transferred to a culture tank. The cells were cultured for about 11 days at a temperature range of 34 to 37° C., while the medium was stirred with an impeller at a rate of 89 rpm, and the dissolved oxygen saturation of the medium was kept at about 40%. During the culture period, cell number, cell viability, and glucose and lactate concentrations of the medium were monitored. When the glucose concentration of the medium became less than 15 mmol/L, the glucose solution was immediately added to the medium so that the glucose concentration became 38 mmol/L. After completion of the culture, the medium was collected. The recovered medium was filtered with Millistak+HC Pod Filter grade D0HC (Merck Inc.) and further filtered with Millistak+HCgrade X0HC (Merck Inc.) to obtain a culture supernatant containing I2S-anti-hTfR antibody 3. The culture supernatant was subjected to ultrafiltration using a Pellicon™ 3 Cassette w/Ultracel PLCTK Membrane (pore size: 30 kDa, membrane area: 1.14 $m^2$, Merck Inc.) and concentrated until the liquid volume was about 1/17. The concentrate was then filtered using OpticapXL600 (0.22 µm, Merck Inc.). The obtained solution was used as a concentrated culture supernatant.

Example 4

Inactivation of the Virus

To the concentrated culture supernatant obtained in Example 3, tri-n-butyl phosphate (TNBP) and polysorbate 80 were added so that the final concentrations were 0.3% (v/v) and 1% (w/v), respectively, and gently stirred at room temperature for 4 hours. This process is conducted for inactivating the virus contaminating the culture supernatant. However, insofar as the culture is carried out using a serum-free medium not containing biological components, there is little possibility that viruses harmful to the human body are contaminated in the culture supernatant.

Example 5

Purification of hI2S-Anti-hTfR Antibodies

The concentrated culture supernatant after inactivation of viruses was added with 0.5 column volume of 20 mM Tris-HCl buffer solution (pH 7.0) containing 140 mM NaCl, and then filtered through Millipak-200 Filter Unit (pore size: 0.22 μm, Merck). The filtered solution was loaded onto a MabSelect SuRe LX column (column volume: about 3.2 L, bed height: about 20 cm, GE Healthcare) which was a Protein A affinity column, equilibrated with 20 mM Tris-HCl buffer (pH 7.0) containing 4 column volumes of 140 mM NaCl, at a constant flow rate of 200 cm/hour, and I2S-anti-hTfR antibody 3 was adsorbed onto Protein A.

Subsequently, the column was washed with 5 column volumes of 10 mM Tris-HCl buffer (pH 7.0) containing 500 mM NaCl and 450 mM arginine at the same flow rate. Then the column was further washed with 2.5 column volumes of 20 mM Tris-HCl buffer (pH 7.0) containing 140 mM NaCl at the same flow rate. Then I2S-anti-hTfR antibody 3 adsorbed to Protein A was eluted with 5 column volumes of 100 mM glycine buffer (pH 3.5) containing 140 mM NaCl. The eluate was immediately neutralized by receiving it in a container containing 1 M Tris-HCl buffer (pH 7.5) in advance.

To the above eluate from the Protein A affinity column, 200 mM phosphate buffer (pH 7.0), 10 mM MES buffer (pH 7.3) containing 4 M NaCl and 2 mM phosphate buffer, and 1 M Tris-HCl buffer solution (pH 8.0) were added in the order, and the concentrations of sodium phosphate and NaCl contained in the eluate were adjusted to 2 mM and 215 mM, respectively, and the pH of the eluate was adjusted to 7.3. The eluate was then filtered through Opticap XL 600 (pore size: 0.22 μm, Merck Inc.). The solution after filtration was applied to a CHT Type II 40 μm column, a hydroxyapatite column (Column volume: about 3.2 L, bed height: about 20 cm, Bio-Rad Inc.), equilibrated with 4 column volumes of 10 mM MES buffer solution (pH 7.3) containing 215 mM NaCl and 2 mM sodium phosphate at a constant flow rate of 200 cm/hour to adsorb I2S-anti-hTfR antibody 3 to hydroxyapatite.

Subsequently, the column was washed with 5 column volumes of the same buffer at the same flow rate. Then I2S-anti-hTfR antibody 3 adsorbed on hydroxyapatite was eluted with 5 column volumes of 35 mM phosphate buffer (pH 7.3) containing 215 mM NaCl. Purification by the hydroxyapatite column was carried out twice using half volume of the eluate from the protein A affinity column.

To the above eluate from the hydroxyapatite column, dilute hydrochloric acid was added to adjust the pH to 6.5. Then, ultrafiltration was carried out using Pellicon™ 3 Cassette w/Ultracel PLCTK Membrane (pore size: 30 kDa, membrane area: 1.14 m², Merck Inc.) to concentrate I2S-antihTfR antibody 3 in the solution at the concentration of about 2 mg/mL. The concentrate was then filtered using Opticap XL 600 (0.22 μm, Merck Inc.).

The above concentrated solution was applied to a Superdex 200 column, size exclusion column (column volume: about 12.6 L, bed height: 40 cm, GE Healthcare Inc.) equilibrated with 5 column volumes of 20 mM phosphate buffer (pH 6.5) containing 0.8 mg/mL NaCl and mg/mL sucrose at a constant flow rate of 19 cm/hour, and the same buffer was supplied at the same flow rate. At this time, an absorbance photometer for continuously measuring the absorbance of the eluate was placed in the flow path of the eluate from the size exclusion column, and the absorbance at 280 nm was monitored. The fractions which corresponded to an absorption peak at 280 nm were collected as a fractions containing I2S-anti-hTfR antibody 3, which was designated as a purified product of I2S-anti-hTfR antibody. Purification on the size exclusion column was carried out twice using half volume of the eluate from the hydroxyapatite column.

Example 6

Study of the Stability of Aqueous Pharmaceutical Compositions Containing I2S-Anti-hTfR Antibody: 1

The purified I2S-anti-hTfR antibody obtained in Example 5 was used to prepare seven aqueous pharmaceutical compositions shown in Table 1, which contained sodium chloride, phosphate buffer, sucrose and poloxamer 188, and I2S-anti-hTfR antibody and differed each other only in the concentrations of poloxamer 188. These seven aqueous pharmaceutical compositions (Formulations A-G) were filled into glass vials in 1 ml each, sealed, and shaken continuously for 6 or 24 hours at room temperature using a shaker (SR-2S, Titec Inc.) at a shaking rate of 240 rounds/minute and amplitudes of 40 mm. The numbers of particles (particle size: 1 to 100 μm) per unit liquid volume (200 μL) contained in the aqueous pharmaceutical composition after shaking was measured by the method described in Example 8. The content of polymers of I2S-anti-hTfR antibodies in the aqueous pharmaceutical compositions after shaking was also determined as described in Example 9.

The results of the determination of the number of particles contained in the aqueous pharmaceutical composition are shown in FIG. 1-1. When the concentration of the poloxamer 188 was 0.1 mg/mL or less, it was found that the number of particles having a particle diameter of 1 to 100 μm contained in the aqueous pharmaceutical composition was greatly increased both after 6 hours and after 24 hours of shaking, as compared with the case where the concentration of the poloxamer 188 was 0.25 mg/mL or more. Furthermore, when the concentration of poloxamer 188 ranged from 0.25 mg/mL to 5 mg/mL, when the concentration of poloxamer 188 was 0.25 mg/mL and 5 mg/mL, the number of particles with a particle size of 1 μm to 100 μm contained in the aqueous pharmaceutical composition tended to increase compared to when the concentration of poloxamer 188 was 0.5 to 2.5 mg/mL (FIG. 1-2). In particular, the number of particles after 24 hours of shaking was minimized when the concentration of poloxamer 188 was 1 mg/mL. These results indicate that the optimal concentrations of poloxamer 188 to prevent the production of particles of 1-100 μm in size are approximately 1 mg/mL.

The results of measuring the amount of the polymers of the I2S-anti-hTfR antibodies contained in aqueous pharmaceutical compositions are described below. The results of the measurement are shown in FIG. 2. When the concentration of poloxamer 188 was greater than 1 mg/mL, polymer was scarcely formed in the aqueous pharmaceutical compositions after both 6 and 24 hours of shaking. When the concentration of poloxamer 188 was 0.5 mg/mL, the amount of polymer after 6 hours and 24 hours of shaking was no more than about 0.028% and about 0.15%, respectively. However, when the concentration of poloxamer 188 was 0.25 mg/mL, the amount of polymer at 6 hours and 24 hours after shaking rapidly increased to about 0.24% and about 0.5%, respectively. When the concentration of the poloxamer 188 was 0.1 mg/mL, the amount of polymer was further increased compared to when the concentration of the poloxamer 188 was 0.25 mg/mL. These results indicate that the optimal concentration of poloxamer 188 to prevent polymer formation after 6 and 24 hours of shaking is 0.5 mg/mL or more, particularly 1.0 mg/mL or more.

From the above results, it is concluded that the concentration of poloxamer 188 in the aqueous pharmaceutical composition effective to suppress the generation of polymers of I2S-anti-hTfR antibodies is 1 mg/mL or more. However, since the aqueous pharmaceutical composition is to be administered to humans as a drug, it is preferable that the concentration of poloxamer 188 is set low. Taking these into consideration, it is concluded that the preferred concentration of poloxamer 188 in the aqueous pharmaceutical composition is in the range of 0.15 to 3 mg/mL, and the more preferred concentration is in the range of 0.3 to 2 mg/mL.

TABLE 1

Composition of aqueous pharmaceutical compositions containing I2S-anti hTfR antibody (the concentration of each additive is shown in mg/mL)

| Ingredients | Formulation A | Formulation B | Formulation C | Formulation D | Formulation E | Formulation F | Formulation G |
|---|---|---|---|---|---|---|---|
| I2S-anti hTfR antibody | 5 | 5 | 5 | 5 | 5 | 5 | 5 |
| Sodium chloride | 0.8 | 0.8 | 0.8 | 0.8 | 0.8 | 0.8 | 0.8 |
| Sodium dihydrogenphosphate dihydrate | 2.14 | 2.14 | 2.14 | 2.14 | 2.14 | 2.14 | 2.14 |
| Dibasic sodium phosphate hydrate | 2.26 | 2.26 | 2.26 | 2.26 | 2.26 | 2.26 | 2.26 |
| Sucrose | 68 | 68 | 68 | 68 | 68 | 68 | 68 |
| Poloxamer 188 | 0.05 | 0.10 | 0.25 | 0.5 | 1.0 | 2.5 | 5.0 |
| pH | 6.5 | 6.5 | 6.5 | 6.5 | 6.5 | 6.5 | 6.5 |

Example 7

Study of the Stability of Aqueous Pharmaceutical Compositions Containing I2S-Anti-hTfR Antibody: 2

The purified I2S-anti-hTfR antibody obtained in Example 5 was used to prepare three aqueous pharmaceutical compositions (formulations H-J) containing sodium chloride, phosphate buffer, sucrose and poloxamer 188, and I2S-anti-hTfR antibody, but differing each other in pH, as shown in Table 2. In addition, three aqueous pharmaceutical compositions (formulations K-M) were prepared which contained I2S-anti-hTfR antibodies and poloxamer 188 at half the concentrations of formulations H-J. These aqueous pharmaceutical compositions were filled into glass vials at a volume of 2 mL for formulations H-J and 4 mL for formulations K-M, sealed, and allowed to stand in the dark for one week at 5° C., for one week at 25° C., for one week at 40° C., and 24 hours at 50° C. The amount of polymers of I2S-anti-hTfR antibodies contained in the respective aqueous pharmaceutical compositions was then determined as described in Example 9. In addition, the amount of degradation products of I2S-anti-hTfR antibodies contained in the respective aqueous pharmaceutical compositions was determined by the methods described in Example 10.

Figure 3:
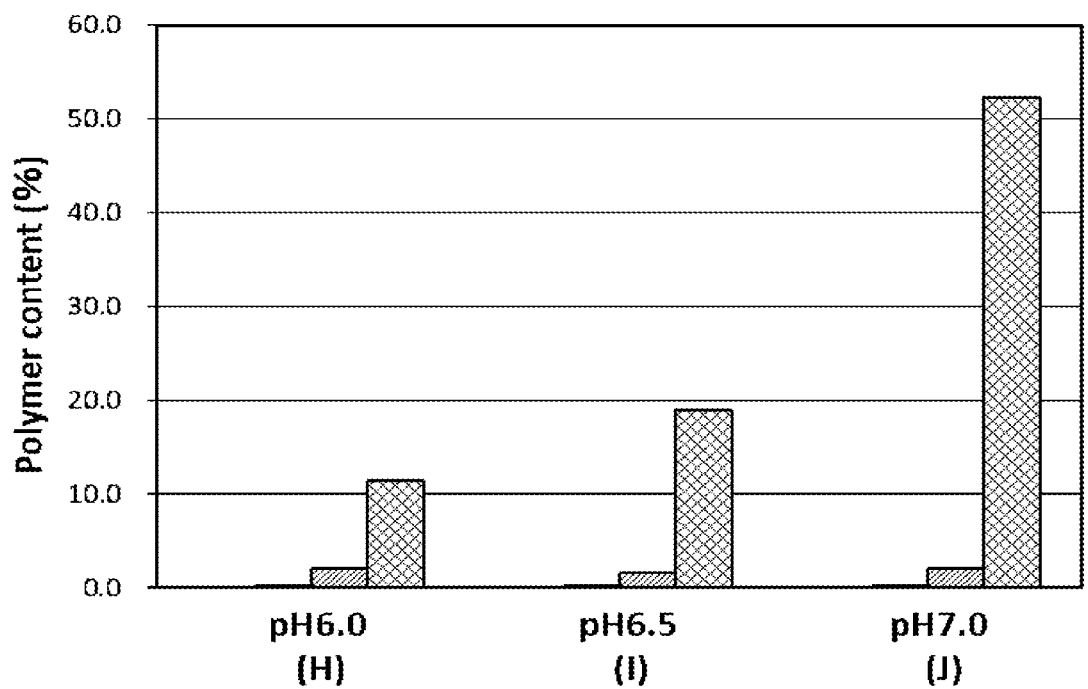
FIG. 3 shows the amount of polymers of I2S-anti-hTfR antibodies in Formulation H (pH 6.0), Formulation I (pH 6.5) and Formulation J (pH 7.0). The bars represent the amount of polymers in Formulations H to J after standing at 5° C. for 1 week (white bar), at 25° C. for 1 week (black bar), at 40° C. for 1 week (hatched bar), and at 50° C. for 24 hours (shaded bar), respectively. The vertical axis represents the polymer content (%).
Figure 4:
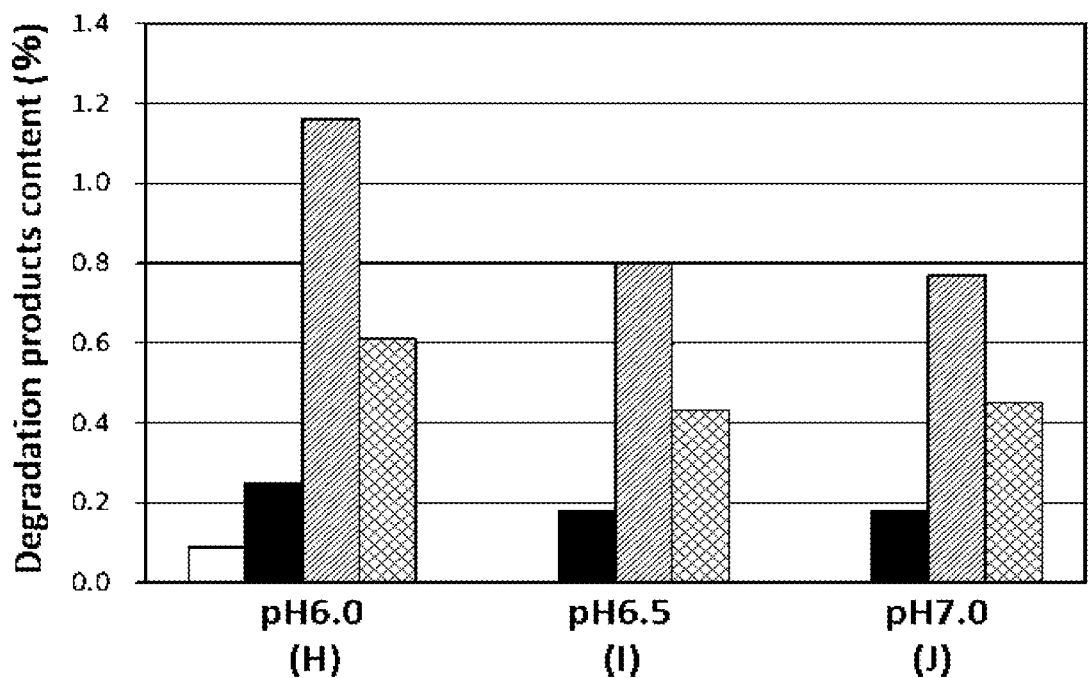
FIG. 4 shows the amount of degradation products of I2S-anti-hTfR antibodies in Formula H (pH 6.0), Formula I (pH 6.5) and Formula J (pH 7.0). The bars represent the amount of degradation products in Formulations H to J after standing at 5° C. for 1 week (white bar), at 25° C. for week (black bar), at 40° C. for 1 week (hatched bar), and at 50° C. for 24 hours (shaded bar), respectively. The vertical axis represents the amount of degradation products (%).

The measured results of the amount of polymers and degradation products of I2S-anti-hTfR antibodies contained in aqueous pharmaceutical compositions for formulations H-J are shown in FIGS. 3 and 4, respectively. The amount of polymers of I2S-anti-hTfR antibodies tended to increase as the pH increased in the range from pH 6 to 7, (FIG. 3). On the other hand, the amount of degradation products of I2S-anti-hTfR antibodies tended to decrease as the pH increased as shown in FIG. 4.

Figure 5:
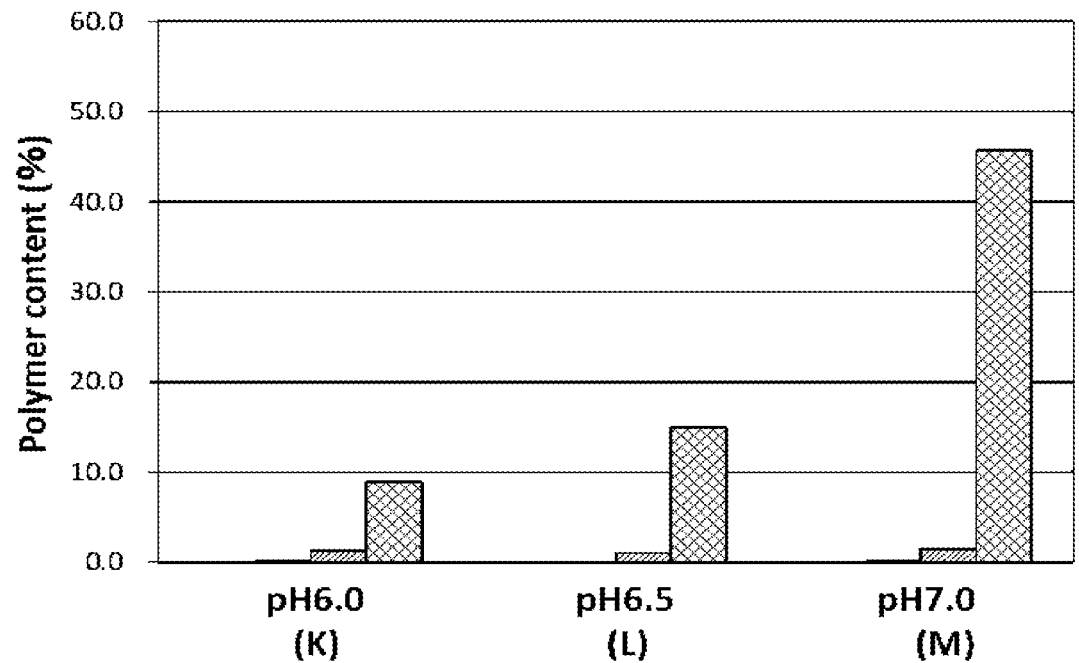
FIG. 5 shows the amount of polymers of I2S-anti-hTfR antibodies in Formulation K (pH 6.0), Formulation L (pH 6.5) and Formulation M (pH 7.0). The bars represent the amount of polymers of I2S-anti-hTfR antibodies in Formulations K to M after standing at 5° C. for 1 week (white bar), at 25° C. for 1 week (black bar), at 40° C. for 1 week (hatched bar), and at 50° C. for 24 hours (shaded bar), respectively. The vertical axis represents the amount of polymer (%).
Figure 6:
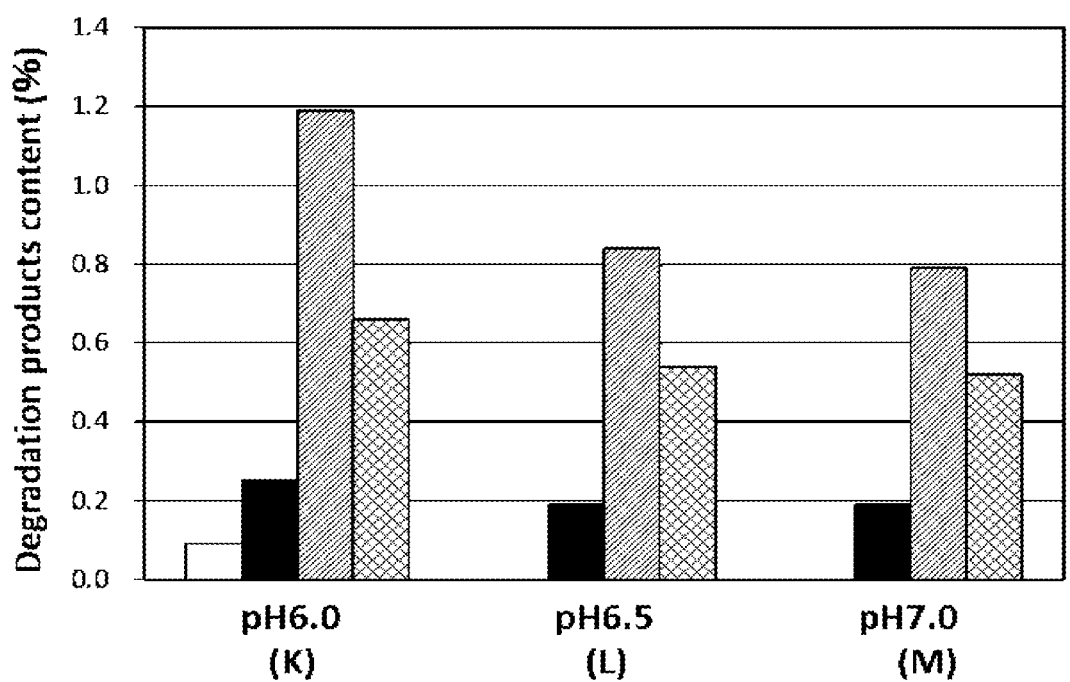
FIG. 6 shows the amount of degradation products of I2S-anti-hTfR antibodies in Formula K (pH 6.0), Formula L (pH 6.5) and Formula M (pH 7.0). The bars represent the content of degradation products in Formulations K to M after standing at 5° C. for 1 week (white bar), at 25° C. for 1 week (black bar), at 40° C. for 1 week (hatched bar), and the at 50° C. for 24 hours (shaded bar), respectively. The vertical axis represents the amount of degradation products (%).

The measured results of the amount of polymers and degradation products of I2S-anti-hTfR antibodies contained in aqueous pharmaceutical compositions for formulations K-M are shown in FIGS. 5 and 6, respectively. As the same with formulations H-J, for formulations K-M, the amount of polymers of I2S-anti-hTfR antibodies tended to increase as the pH increased in the range from pH 6 to 7 (FIG. 5), while the content of degradation products of I2S-anti-hTfR antibodies tended to decrease as the pH increased (FIG. 6).

As shown in the above results, when the pH of the aqueous pharmaceutical composition is pH 7, the amount of the polymers tends to increase if compared with the case where the pH is pH 6 or 6.5. And when the pH of the aqueous pharmaceutical composition is pH 6, the amount of degradation products tends to increase if compared with the case where the pH is pH 6.5 or 7. It is therefore concluded that the optimal pH of the aqueous pharmaceutical compositions effective to suppress the production of polymers of I2S-anti-hTfR antibodies and to suppress the degradation of I2S-anti-hTfR antibodies is approximately pH 6.5.

TABLE 2

Composition of aqueous pharmaceutical compositions containing I2S-anti hTfR antibody (the concentration of each additive is shown in mg/mL)

| Ingredients | Formulation H | Formulation I | Formulation J | Formulation K | Formulation L | Formulation M |
|---|---|---|---|---|---|---|
| I2S-anti hTfR antibody | 5 | 5 | 5 | 2.5 | 2.5 | 2.5 |
| Sodium chloride | 0.8 | 0.8 | 0.8 | 0.8 | 0.8 | 0.8 |
| Sodium dihydrogenphosphate dihydrate | 2.74 | 2.14 | 1.13 | 2.74 | 2.14 | 1.13 |
| Dibasic sodium phosphate hydrate | 0.88 | 2.26 | 3.12 | 0.88 | 2.26 | 3.12 |
| Sucrose | 75 | 75 | 75 | 75 | 75 | 75 |
| Poloxamer 188 | 0.65 | 0.65 | 0.65 | 0.325 | 0.325 | 0.325 |
| pH | 6.0 | 6.5 | 7.0 | 6.0 | 6.5 | 7.0 |

Example 8

Measurement of the Number of Particles (Particle Size: 1 to 100 μm) Contained in Aqueous Pharmaceutical Compositions The measurement of the number of particles contained in aqueous pharmaceutical compositions was carried out using a FlowCAM™ (Fluid Imaging Technologies), which is a flow imaging particle analyzer. The flow imaging particle analyzer is a device capable of measuring the number of particles contained in a sample solution by drawing a sample solution into a flow cell orthogonal to an optical system by a syringe pump and photographing particles passing through the flow cell in real time. The measurement was performed by setting the particle size to be detected to 1 to 100 μm.

Example 9

Measurement of the Amount of Polymers of I2S-Anti-hTfR Antibodies in Aqueous Pharmaceutical Compositions A TSKgel UltraSW Aggregate 3 μm column (7.8 mm diameter×30 cm length, TOSOH Inc.), which was a size-exclusion column chromatography column, was set in the Shimadzu HPLC System LC-20A (Shimazu). In addition, an absorption photometer was installed downstream of the column so that the absorbance (measurement wavelength 215 nm) of the effluent from the column could be measured continuously. After equilibrating the column with 0.2 M sodium phosphate buffer, a sample solution containing 3-20 μg of I2S-anti-hTfR antibody was loaded onto the column and 0.2 M sodium phosphate buffer was supplied at a flow rate of 0.5 mL/min. During this period, the elution profile was obtained by measuring the absorbance (measurement wavelength 215 nm) of the effluent from the column. The peak area of the monomer of the I2S-anti-hTfR antibody (monomer peak area), and the peak area of the polymer of I2S-anti-hTfR antibodies (polymer peak area), the peak of the polymer appearing earlier than the monomer peak, were obtained from the obtained elution profiles. The polymer amount (%) was determined by the following formula.

Polymer amount (%)=(polymer peak area)/(monomer peak area+polymer peak area)×100

Example 10

Determination of the Content of Degradation Products of I2S-Anti-hTfR Antibodies in Aqueous Pharmaceutical Compositions A TSKgel UltraSW Aggregate 3 μm column (7.8 mm diameter×30 cm length, TOSOH Inc.), which was a size-exclusion column chromatography column, was set in the Shimadzu HPLC System LC-20A (Shimazu). In addition, an absorption photometer was installed downstream of the column so that the absorbance (measurement wavelength 215 nm) of the effluent from the column could be measured continuously. After equilibrating the column with 0.2 M sodium phosphate buffer, a sample solution containing 3-20 μg of I2S-anti-hTfR antibody was loaded onto the column and 0.2 M sodium phosphate buffer was supplied at a flow rate of 0.5 mL/min. During this period, the elution profile was obtained by measuring the absorbance (measurement wavelength 215 nm) of the effluent from the column. The peak area of the monomer of the I2S-anti-hTfR antibody (monomer peak area), and the peak area of degradation products of I2S-anti-hTfR antibodies (degradation products peak area), the peak of the polymer appearing earlier than the monomer peak, were obtained from the obtained elution profiles. The degradation products content (%) was determined by the following formula.

The degradation products amount (%)=(degradation products peak area)/(monomer peak area+degradation products peak area)×100

Example 11

Formulation Design of Aqueous Pharmaceutical Compositions

Based on the results of the studies given in Examples 6 and 7 above, examples of formulations of aqueous pharmaceutical compositions that contain I2S-anti-hTfR antibodies can be designed to have the compositions shown in Table 3, Formulations O and P. These aqueous pharmaceutical compositions are filled and sealed in glass or plastic vials, ampoules, or syringes in a volume of 1-10 mL and stored at a low temperature, e.g., 4° C. Those filled and enclosed in syringes will be a prefilled-type syringe preparation.

TABLE 3

Examples of aqueous pharmaceutical compositions containing I2S-anti hTfR antibody

| Ingredients | Formulation O | Formulation P |
|---|---|---|
| I2S-anti hTfR antibody | 5 | 2.5 |
| Sodium chloride | 0.8 | 0.8 |
| Sodium dihydrogenphosphate dihydrate | 2.14 | 2.14 |
| Dibasic sodium phosphate hydrate | 2.26 | 2.26 |
| Sucrose | 75 | 75 |
| Poloxamer 188 | 0.65 | 0.325 |
| pH | 6.5 | 6.5 |

INDUSTRIAL APPLICABILITY

According to the present invention, an aqueous pharmaceutical composition containing a protein in which an antibody and a lysosomal enzyme are linked as an active ingredient can be stably provided to the market.

SEQUENCE LISTING FREE TEXT

SEQ ID NO:2: Amino acid sequence of the light-chain of humanized anti-hTfR antibody No. 1

SEQ ID NO:3: Nucleotide sequence encoding amino acid sequence of the light-chain of humanized anti-hTfR antibody No. 1, synthetic sequence SEQ ID NO:4: Amino acid sequence of the light-chain of humanized anti-hTfR antibody No. 2

SEQ ID NO:5: Nucleotide sequence encoding amino acid sequence of the light-chain of humanized anti-hTfR antibody No. 2, synthetic sequence SEQ ID NO:6: Amino acid sequence of the light-chain of humanized anti-hTfR antibody No. 3

SEQ ID NO:7: Nucleotide sequence encoding amino acid sequence of the light-chain of humanized anti-hTfR antibody No. 3, synthetic sequence SEQ ID NO:8: Amino acid sequence of the heavy-chain of humanized anti-hTfR antibody No. 1
SEQ ID NO:9: Amino acid sequence of the heavy-chain of humanized anti-hTfR antibody No. 2
SEQ ID NO:10: Amino acid sequence of the heavy-chain of humanized anti-hTfR antibody No. 3
SEQ ID NO:11: Primer Hyg-Sfi5', synthetic sequence
SEQ ID NO:12: Primer Hyg-BstX3', synthetic sequence
SEQ ID NO:13: Amino acid sequence of fused protein of the heavy-chain of humanized anti-hTfR antibody No. 1 and hI2S
SEQ ID NO:14: Nucleotide sequence encoding amino acid sequence of fused protein of the heavy-chain of humanized anti-hTfR antibody No. 1 and hI2S, synthetic sequence
SEQ ID NO:15: Amino acid sequence of fused protein of the heavy-chain of humanized anti-hTfR antibody No. 2 and hI2S
SEQ ID NO:16: Nucleotide sequence encoding amino acid sequence of fused protein of the heavy-chain of humanized anti-hTfR antibody No. 2 and hI2S, synthetic sequence
SEQ ID NO:17: Amino acid sequence of fused protein of the heavy-chain of humanized anti-hTfR antibody No. 3 and hI2S
SEQ ID NO:18: Nucleotide sequence encoding amino acid sequence of fused protein of the heavy-chain of humanized anti-hTfR antibody No. 3 and hI2S, synthetic sequence
SEQ ID NO:19: Amino acid sequence of an exemplified linker 1
SEQ ID NO:20: Amino acid sequence of an exemplified linker 2
SEQ ID NO:21: Amino acid sequence of an exemplified linker 3
SEQ ID NO:23: Amino acid sequence of the light-chain variable region of humanized anti-hTfR antibody No. 1
SEQ ID NO:24: Amino acid sequence of the heavy-chain variable region of humanized anti-hTfR antibody No. 1
SEQ ID NO:25: Amino acid sequence of the light-chain variable region of humanized anti-hTfR antibody No. 2
SEQ ID NO:26: Amino acid sequence of the heavy-chain variable region of humanized anti-hTfR antibody No. 2
SEQ ID NO:27: Amino acid sequence of the light-chain variable region of humanized anti-hTfR antibody No. 3
SEQ ID NO:28: Amino acid sequence of the heavy-chain variable region of humanized anti-hTfR antibody No. 3

SEQUENCE LISTING

1208JP_ST25.txt

The invention claimed is:

1. A stable aqueous pharmaceutical composition, comprising:
   a fusion protein of an anti-human transferrin receptor antibody and human iduronate-2-sulfatase at a concentration of 5 mg/mL;
   sodium chloride at a concentration of from 0.7 to 0.9 mg/mL;
   sucrose at a concentration of from 70 to 80 mg/mL;
   polyoxyethylene (160) polyoxypropylene (30) glycol at a concentration of from 0.3 to 0.8 mg/mL; and,
   a phosphate buffer at a concentration of from 15 to 25 mM,
   wherein the aqueous pharmaceutical composition has a pH of from 6.2 to 6.8, and
   wherein the fusion protein comprises a light chain of the anti-human transferrin receptor antibody and a conjugate of a heavy chain of the anti-human transferrin receptor antibody with the human iduronate-2-sulfatase, and in the conjugate the human iduronate-2-sulfatase is linked at the C-terminal side of the heavy chain of the anti-human transferrin receptor antibody via a linker having the amino acid sequence of Gly-Ser, and wherein the conjugate has the amino acid sequence of SEQ ID NO:17 and the light chain has the amino acid sequence of SEQ ID NO:6.

* * * * *